United States Patent [19]

Awaya et al.

[11] Patent Number: 5,304,555

[45] Date of Patent: Apr. 19, 1994

[54] PYRIMIDINES AND PHARMACEUTICALLY ACCEPTABLE SALTS THEREOF USEFUL IN TREATMENT OF NEUROLOGICAL DISORDERS

[75] Inventors: Akira Awaya, Yokohama; Kazutoshi Horikomi, Mobara; Tadayuki Sasaki, Mobara; Hisashi Kobayashi, Mobara; Akira Mizuchi, Mobara; Takuo Nakano, Yokohama; Ikuo Tomino, Ohtake; Shintaro Araki, Yamaguchi; Mitsuyuki Takesue, Iwakuni; Koji Kato, Yamaguchi; Keiichi Yokoyama, Iwakuni, all of Japan

[73] Assignees: Mitsui Petrochemical Industries, Ltd.; Mitsui Pharmaceuticals, Inc., both of Tokyo, Japan

[21] Appl. No.: 600,171

[22] Filed: Oct. 19, 1990

Related U.S. Application Data

[63] Continuation-in-part of Ser. No. 347,892, Apr. 25, 1989, abandoned.

[30] Foreign Application Priority Data

Aug. 26, 1987 [JP] Japan .................. 62-210170

[51] Int. Cl.$^5$ ............... C07D 279/12; A61K 31/54
[52] U.S. Cl. ................ 514/228.5; 514/211; 514/218; 514/227.8; 514/228.2; 514/234.2; 514/235.8; 514/252; 514/254; 514/258; 514/275; 540/575; 540/600; 544/58.6; 544/117; 544/122; 544/280; 544/295; 544/324
[58] Field of Search ........... 544/58.6, 117, 122, 544/280, 295, 324; 514/227.8, 228.2, 228.5, 234.2, 235.8, 252, 254, 258, 275

[56] References Cited

U.S. PATENT DOCUMENTS

| | | | |
|---|---|---|---|
| 4,215,216 | 7/1980 | Scotese et al. | 544/117 |
| 4,698,091 | 10/1987 | Brunner et al. | 71/87 |
| 4,742,165 | 5/1988 | Yokoyama et al. | 540/205 |
| 4,788,195 | 11/1988 | Torley et al. | 514/252 |
| 4,959,368 | 9/1990 | Awaya et al. | 514/252 |
| 4,975,530 | 12/1990 | Tzikas et al. | 534/633 |
| 5,075,308 | 12/1991 | Ishikawa et al. | 514/252 |

FOREIGN PATENT DOCUMENTS

| | | | |
|---|---|---|---|
| 188094 | 7/1986 | European Pat. Off. | 514/258 |
| 0257102 | 2/1988 | European Pat. Off. | |
| 358428 | 7/1957 | Switzerland | 514/258 |

OTHER PUBLICATIONS

Journal of Chemical Society, 1172-78 (1967).
CA 86: 121363e (1977).
Kobayashi et al, Japan Kokai 76:100,008 Chemical Abstracts vol. 86, 1977 Abstrract 121363e.
Granik, et al Khim. Geterotsikl. Soedin. 1978 (12) 1671-6 Chem. Abs. vol. 90, 1979 Abstract 121530a.
Sicho, et al Sb. Vys. Sk. Chem. Technol. Praze, Potraviny 1973 E40, 29-40 Chem. Abs. vol. 83, 1975, Abstract 22902m.
Shadbolt, et al J. Chem. Soc. (C) 2967 pp. 1172-1178.

Primary Examiner—Paul R. Michl
Assistant Examiner—Jyothsna Venkat
Attorney, Agent, or Firm—Sherman and Shalloway

[57] ABSTRACT

This invention provides novel pyrimidines or their pharmaceutically acceptable salts thereof and process for preparation thereof. The novel compounds are useful for neurological diseases of the peripheral and central nervous systems of animals.

24 Claims, No Drawings

PYRIMIDINES AND PHARMACEUTICALLY ACCEPTABLE SALTS THEREOF USEFUL IN TREATMENT OF NEUROLOGICAL DISORDERS

This is a continuation-in-part of application Ser. No. 07/347,892, filed Apr. 25, 1989, now abandoned.

TECHNICAL FIELD

This invention relates to novel pyrimidines or their pharmaceutically acceptable salts thereof, and novel therapeutic agents for neurological diseases of the peripheral and central nervous systems of animals containing the above compounds as active ingredients.

BACKGROUND ART

Japanese Patent Publication No. 23,394/1971 discloses that aminopyrimidines represented by the following formula

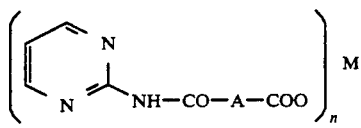

wherein A represents an alkylene group having up to 16 carbon atoms, or a lower alkylene group substituted by an amino group or a $C_{2-5}$ acylamino group, N represents H, Na, K, $NH_4$, Mg, Ca or an organic basic ammonium salt, and n is a value equal to the atomic valency of M, have interesting therapeutic activity, particularly as an anti-melanchoric agent and psychoanaleptic agent in the field of psychosis.

Japanese Patent Publication No. 22044/1976 discloses that dichloro-lower aliphatic carboxylic acid salts of 2-isopropylaminopyrimidine, such as 2-isopropylaminopyrimidine dicloroacetate, are useful as a therapeutic agent for a neurological disease.

Japanese Laid-Open Patent Publication No. 00477/1977 (Patent Publication No. 28548/1984) discloses that 2-isopropylaminopyrimidine phosphate is useful as a therapeutic agent for a neurological disease.

Japanese Patent Publication No. 157575/1979 discloses a process for producing 2-chloropyrimidine in a high yield. A working example in this patent publication describes the preparation of 2-chloropyrimidine in a yield of 69%.

Japanese Laid-Open Patent Publication No. 393/1980 discloses a process for producing 2-isopropylaminopyrimidine in a high yield. A working example of this patent publication describes the preparation of 2-isopropylaminopyrimidine in a yield of 60%.

Japanese Laid-Open Patent Publication No. 122768/1980 discloses that a hydroxy derivative of 2-isopropylaminopyrimidine represented by the following formula

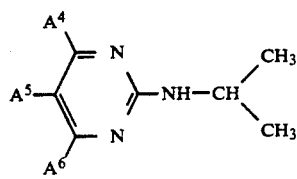

wherein $A^4$, $A^5$ and $A^6$ each represent H or OH, and at least one of them represents OH, is useful in the field of nerve regeneration and for treatment of myodystrophy.

Japanese Laid-Open Patent Publication No. 145670/1980 discloses that 2-isopropylaminohalogenopyrimidines represented by the following formula

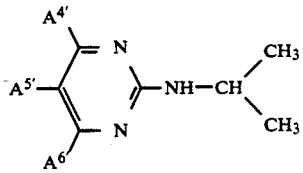

wherein $A_4'$, $A_5'$ and $A_6'$ each represent H or a halogen atom, and at least one of them is a halogen atom, are useful for treatment of various neurological diseases and myodystrophy.

Japanese Laid-Open Patent Publication No. 145,671/1980 discloses a process for producing a hydroxy derivative of 2-isopropylaminopyrimidine.

Japanese Laid-Open Patent Publication No. 151,571/1980 discloses that 2-isopropylamino-5-halogenopyrimidines are interesting in the treatment of neurological diseases.

Japanese Laid-Open Patent Publication No. 10177/1981 discloses a process for producing 2-isopropylaminopyrimidine substantially in a quantitative yield by aminolyzing 2-methylsulfonylpyrimidine with isopropylamine.

Japanese Laid-Open Patent Publication No. 26880/1981 discloses a process for producing 2-isopropylaminopyrimidine which comprises reacting bis-(isopropylguanidine) sulfate with 1,1,3,3-tetraethoxypropane.

Japanese Laid-Open Patent Publication No. 90,013/1981 describes a therapeutic agent for myodystropy, myopathy, muscle rigidity and/or dysfunction of neuro-muscular transmission comprising substituted derivative of pyrimidine or its therapeutically acceptable salt or its metabolite as an active ingredient. However, it merely discloses various salts such as an orthophosphate, of 2-isopropylaminopyrimidine as an active compound.

Japanese Laid-Open-Patent Publication No. 65873/1986 discloses that 2-piperazinopyrimidine derivatives of the following formula

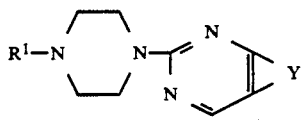

wherein $R^1$ is H or aralkyl, and Y is a divalent organic group defined in the claim of this patent publication, are useful as a herbicide for paddies and upland farms.

The present inventors previously provided a novel therapeutic agent for neurological diseases comprising a specified 2-piperazinopyrimidine derivative or its pharmaceutically acceptable salt (International Laid-Open No. WO87/04928).

DISCLOSURE OF INVENTION

It is an object of this invention to provide novel pyrimidines and their pharmaceutically acceptable salts.

Another object of this invention is to provide therapeutic agents for neurological diseases comprising the above novel compounds.

Another object of this invention is to provide a novel therapeutic agent for neurological diseases having the effect of regenerating and repairing nerve cells.

Another object of this invention is to provide a novel therapeutic agent for neurological diseases which can be applied to disorders of peripheral nerves.

Another object of this invention is to provide a novel therapeutic agent for neurological diseases which can be applied to diseases of central nerves which are different from psychosis and in which abnormality in the operating system or the metabolic system of chemical transmitters is regarded as being primarily involved.

Another object of this invention is to provide a novel therapeutic agent for cerebral diseases which has the effect of improving and restoring learning and memory.

Another object of this invention is to provide a novel therapeutic agent for neurological diseases or cerebral diseases, which comprises a comprehensively excellent and useful compound having pharmacological actions suitable for treatment of neurological diseases or cerebral diseases with little side effects such as liver trouble.

Still other objects of this invention along with its advantages will become apparent from the following description.

According to this invention, the above objects and advantages of the invention are achieved by pyrimidines represented by the following formula (I)

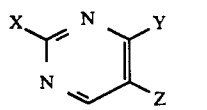  (I)

wherein X represents a group of the following formula (I)-1

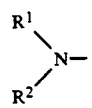  (I)-1 wherein $R^1$ represents a hydrogen atom or an alkyl group having 1 to 4 carbon atoms, $R^2$ represents a phenethyl, cyclohexyl, phenyl, benzyl or piperidyl group or an alkyl group having 1 to 4 carbon atoms which may be substituted by a piperidino group which may be substituted by a $C_{1-4}$ alkyl group, or $R^1$ and $R^2$ together may form a heterocyclic ring selected from the group consisting of

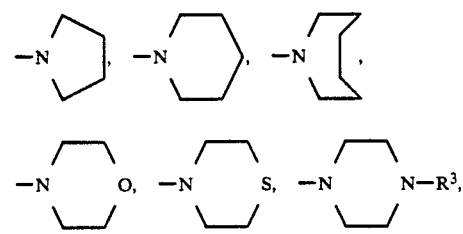

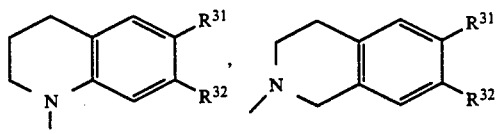

and

together with the nitrogen atom to which they are bonded, $R^3$ represents a cyclohexyl, 4-pyridyl, benzoyl or $C_{1-4}$ alkyl group, a phenyl group which may be substituted by chlorine or a lower alkoxy group, or an alkylaminocarbonyl group mono- or di-substituted by a $C_{1-6}$ alkyl group, and $R^{31}$ and $R^{32}$ are identical or different and each represents a hydrogen atom or a lower alkoxy group, and the heterocyclic group may optionally be substituted by a phenyl, benzyl, phenylthio, cyano or lower alkoxycarbonyl group or monosubstituted by the group

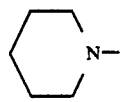

or mono- to penta-substituted by a $C_{1-4}$ alkyl group, or substituted by a $C_{3-5}$ polymethylene group on the adjoining ring-member carbons, or
(ii) a group represented by the following formula (I)-2

$$-S-R^4 \quad (I)\text{-}2$$

wherein $R^4$ represents an alkyl group having 1 to 4 carbon atoms,

Y represents an amino group or a substituted amino group mono- or di-substituted by a $C_{1-4}$ alkyl group, and Z represents a methyl group substituted by a $C_{2-5}$ lower alkoxycarbonyl group or a lower alkoxycarbonyl group having 2 to 5 carbon atoms, or Y and Z together may form a group of the following formula

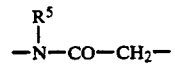

wherein $R^5$ represents an alkyl group having 1 to 4 carbon atoms which may be substituted by a lower alkoxy group, or
a group of the following formula

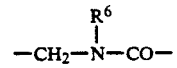

wherein $R^6$ represents an alkyl group having 1 to 4 carbon atoms,
as a divalent group —Y—Z—;

or their pharmaceutically acceptable salts.

In the above formula (I), x is either (i) a group of the following formula (I)-1

$$\begin{matrix} R^1 \\ \phantom{R^1}\diagdown \\ \phantom{RRR}N- \\ \phantom{R^1}\diagup \\ R^2 \end{matrix} \qquad \text{(I)-1}$$

or (ii) a group of the following formula (I)-2

$$-SR^4 \qquad \text{(I)-2}$$

In formula (I)-1, $R^1$ represents a hydrogen atom or an alkyl group having 1 to 4 carbon atoms.

The alkyl group may be linear or branched, and its examples include methyl, ethyl, n-propyl, isopropyl, n-butyl, sec-butyl, iso-butyl and 1-butyl.

In formula (I)-I, $R^2$ represents a phenethyl, cyclohexyl, phenyl, benzyl or piperidyl or a $C_{1-4}$ alkyl group which may be substituted by a piperidino group. The piperidyl group may be substituted by an alkyl group having 1 to 4 carbon atoms. Examples of the lower alkyl group may be the same as given above.

In formula (I)-1, $R^1$ and $R^2$ together may form a heterocyclic ring selected from the group consisting of groups of the following formulae

[structures shown]

and

[structure shown]

together with the nitrogen atom to which they are bonded. These heterocyclic groups may be substituted by a phenyl, benzyl, phenylthio, cyano or lower alkoxycarbonyl group or monosubstituted by the group

[structure shown]

or mono- to penta-substituted by a $C_{1-4}$ alkyl group, or substituted by a $C_{3-5}$ polymethylene group on the adjoining ring-member carbons.

The lower alkoxycarbonyl group preferably has 1 to 4 carbon atoms in the alkoxy moiety. Examples include methoxycarbonyl, ethoxycarbonyl, n-propoxycarbonyl, iso-propoxycarbonyl, n-butoxycarbonyl, isobutoxycarbonyl, sec-butoxycarbonyl and tert-butoxycarbonyl groups.

Examples of the $C_{1-4}$ alkyl group may be the same as those given hereinabove.

The polymethylene group having 3 to 5 carbon atoms includes trimethylene, tetramethylene and pentamethylene groups. These groups may form 5-membered, 6-membered and 7-membered rings respectively together with the adjacent ring-member carbons to which they are bonded.

The substituent $R^3$ at the 4-position of the piperazino group is a cyclohexyl, 4-pyridyl, benzoyl or $C_{1-4}$ alkyl group, or a phenyl group which may be substituted by chlorine or a lower alkoxy group, or an alkylaminocarbonyl group mono- or di-substituted by an alkyl group having 1 to 6 carbon atoms.

The lower alkyl group may be the same as those exemplified hereinabove, and also an n-hexyl group.

The lower alkoxy group preferably has 1 to 4 carbon atoms, and examples are methoxy, ethoxy, n-propoxy, isopropoxy, n-butoxy, isobutoxy, sec-butoxy and tert-butoxy groups.

Examples of the alkylamino group in the alkylaminocarbonyl group are methylamino, ethylamino, n-propylamino, isopropylamino, n-butylamino, t-butylamino, n-pentylamino, n-hexylamino, dimethylamino, diethylamino, di-n-propylamino, ethylamino, di-iso-propylamino, di-n-butylamino and cyclohexylamino groups.

$R^{31}$ and $R^{32}$ in the group

[structure shown]

are identical or different and each represents a hydrogen atom or a lower alkoxy group.

The lower alkyl group preferably has 1 to 4 carbon atoms, and may be the same as exemplified hereinabove.

In formula (I)-2, $R^4$ represents an alkyl group having 1 to 4 carbon atoms, and its examples may be the same as those given hereinabove.

Examples of the group represented by formula (I)-2 are methylthio, ethylthio, n-propylthio, isopropylthio, n-butylthio, sec-butylthio and t-butylthio groups.

In formula (I), Y is an amino group ($-NH_2$) or a substituted amino group mono- or di-substituted with an alkyl group having 1 to 4 carbon atoms.

Specific examples of the $C_{1-4}$ alkyl group and the substituted amino group (alkylamino group) may be the same as those given hereinabove.

In formula (I), Z represents a methyl group substituted by a lower alkoxycarbonyl group having 2 to 5 carbon atoms, or an alkoxycarbonyl group having 2 to 5 carbon atoms. Examples of the lower alkoxycarbonyl group include methoxycarbonyl, ethoxycarbonyl, n-propoxycarbonyl, isopropoxycarbonyl, n-butoxycarbonyl and sec-butoxycarbonyl groups.

In formula (I), Y and Z together may form a group of the formula $$\begin{matrix} R^5 \\ | \\ -N-CO-CH_2- \end{matrix}$$

-continued

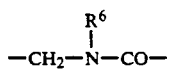

or

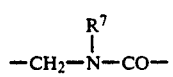

in which each of R⁵, R⁶ and R⁷ represents an alkyl group having 1 to 4 carbon atoms, with the proviso that the lower alkyl group of R⁵ may be substituted by a lower alkoxyl group having 1 to 4 carbon atoms,
as a divalent group —Y—Z—.

Examples of the compounds of formula (I) are shown below.

(A) Compounds of formula (I) in which —Y—Z— represents

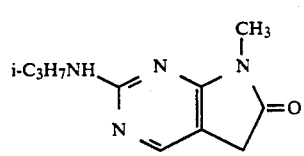  (100)

Hydrochloride of (100)     (102)

Maleate of (100)     (104)

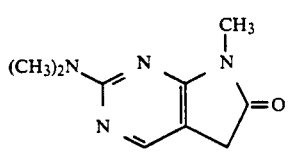 (106)

Maleate of (106)     (108)

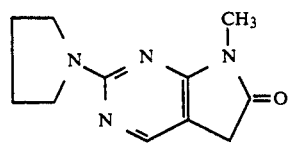 (110)

Maleate of (110)     (112)

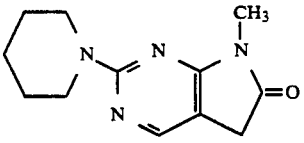 (114)

Hydrochloride of (114)     (116)

Maleate of (114)     (118)

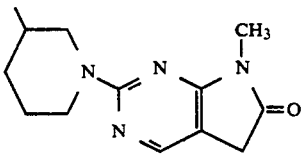 (500)

Hydrochloride of (500)     (502)

-continued

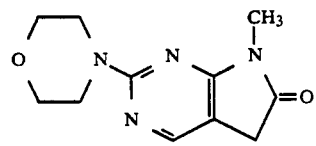 (120)

Hydrochloride of (120)     (122)

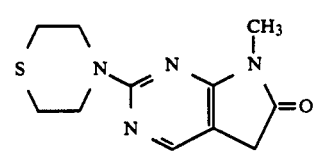 (124)

Hydrochloride of (124)     (126)

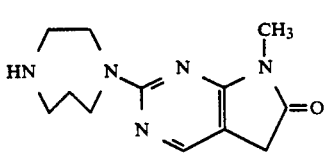 (128)

Hydrochloride of (128)     (129)

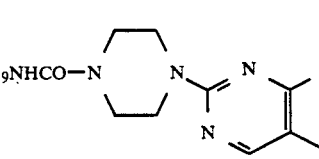 (130)

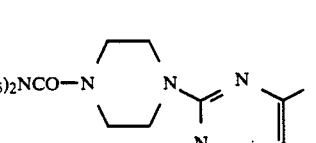 (132)

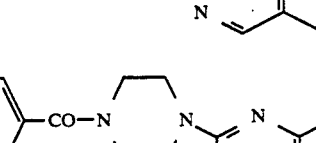 (504)

Hydrochloride of (504)     (506)

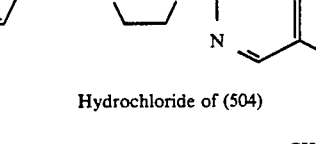 (508)

Hydrochloride of (508)     (510)

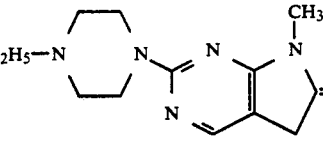 (512)

Hydrochloride of (512)     (514)

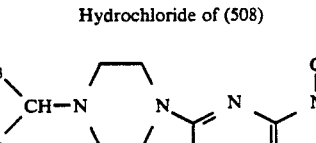 (516)

-continued
Hydrochloride of (516) (518)
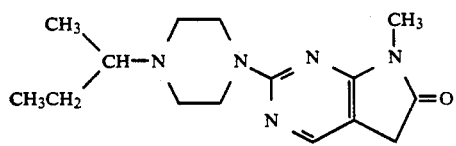 (520)
Hydrochloride of (520) (522)
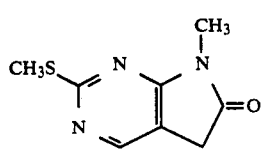 (134)
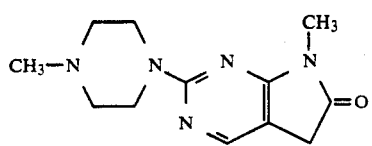 (136)
Maleate of (136) (138)
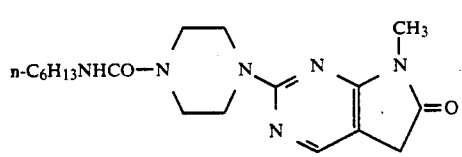 (140)
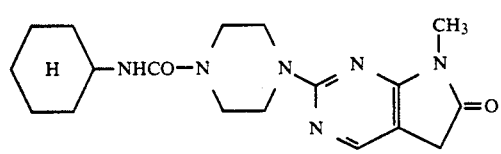 (142)
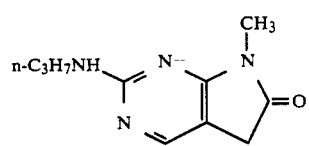 (144)
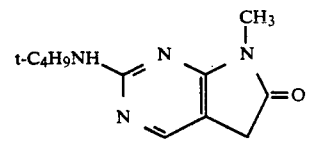 (146)
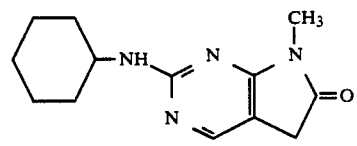 (147)
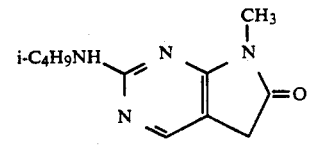 (148)
-continued
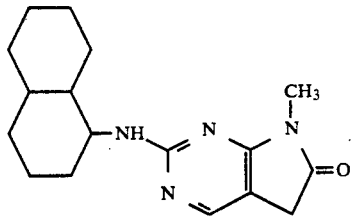 (149)
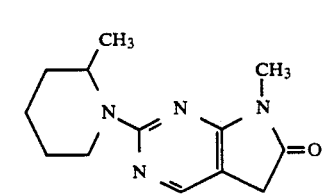 (150)
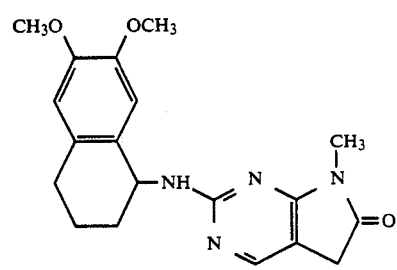 (151)
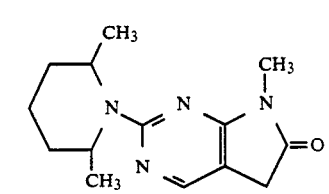 (152)
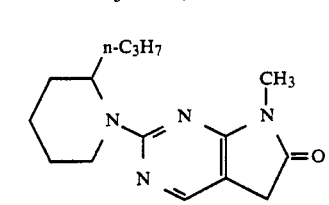 (154)
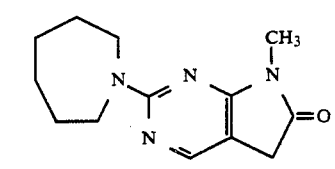 (156)
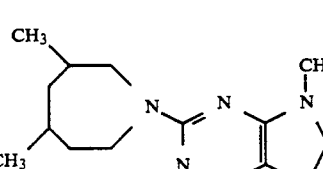 (158)
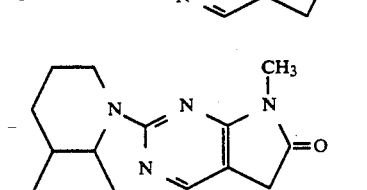 (160)

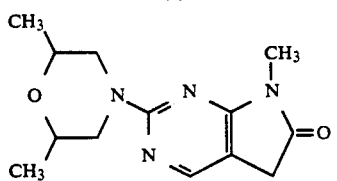 (162)
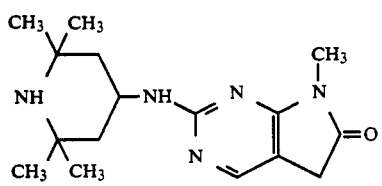 (164)
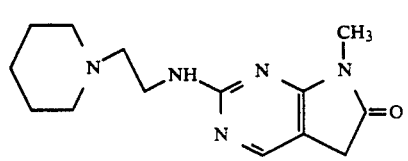 (166)
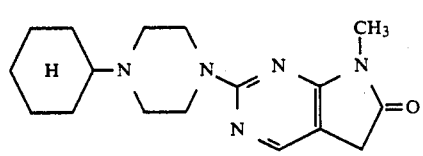 (524)
Hydrochloride of (524) (526)
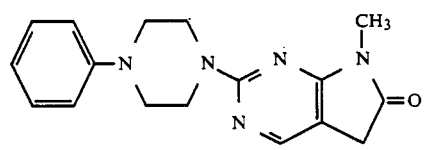 (528)
Hydrochloride of (528) (530)
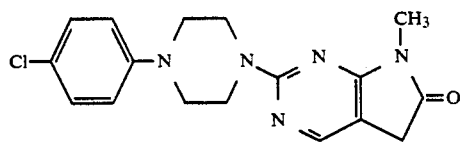 (532)
Hydrochloride of (532) (534)
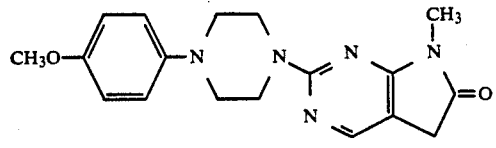 (536)
Hydrochloride of (536) (538)
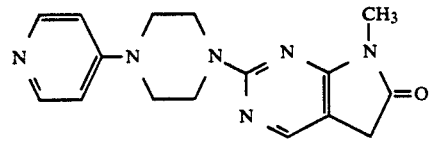 (540)
p-Toluenesulfonate of (540) (542)
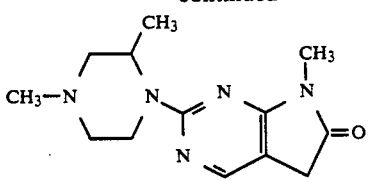 (168)
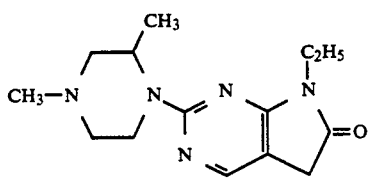 (170)
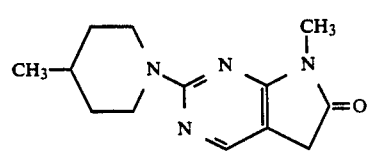 (174)
Hydrochloride of (174) (175)
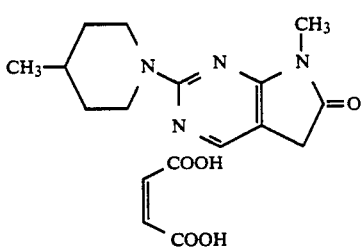 (175-1)
Maleate of (174)
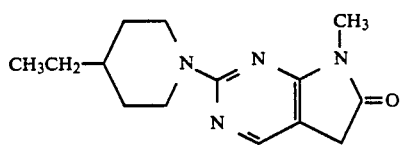 (175-2)
Maleate of (175-2) (175-3)
Hydrochloride of (175-2) (175-4)
Fumarate of (175-2) (175-5)
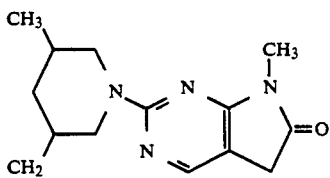 (176)
Hydrochloride of (176) (177)
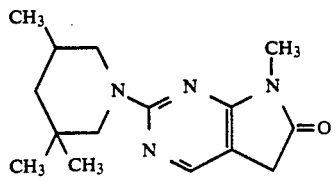 (178)

-continued
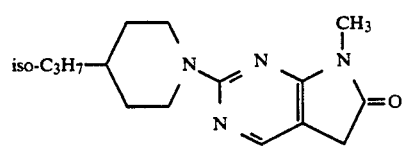 (544)
Hydrochloride of (544) (546)
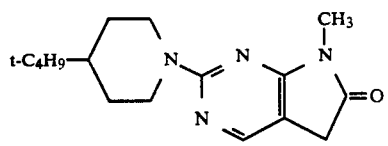 (548)
Hydrochloride of (548) (550)
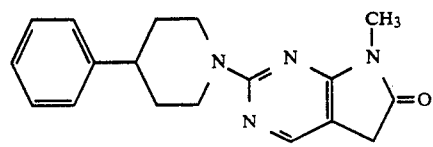 (552)
Hydrochloride of (552) (554)
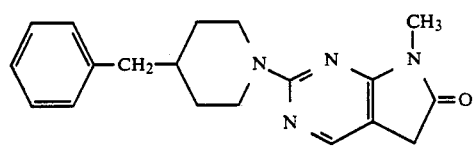 (556)
Hydrochloride of (556) (557)
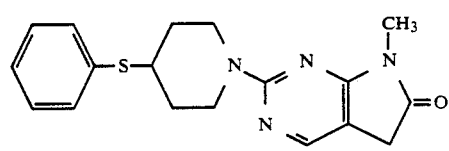 (558)
Hydrochloride of (558) (559)
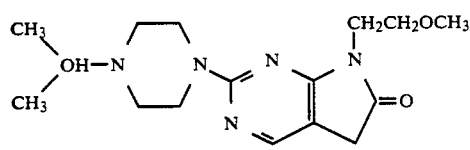 (586)
Hydrochloride of (586) (588)
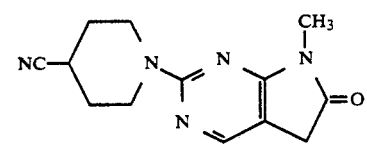 (560)
Hydrochloride of (560) (562)
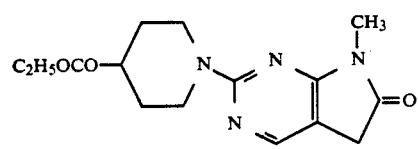 (564)
Hydrochloride of (564) (566)
-continued
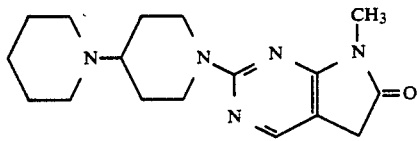 (568)
Hydrochloride of (568) (570)
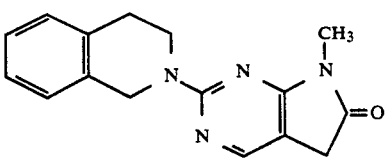 (572)
Hydrochloride of (572) (574)
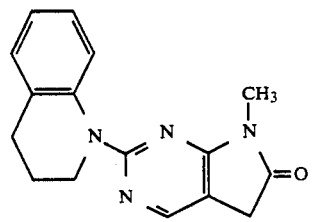 (575)
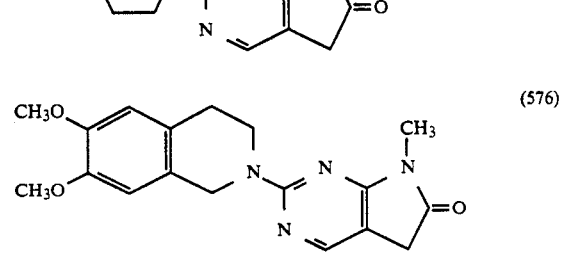 (576)
Hydrochloride of (576) (578)
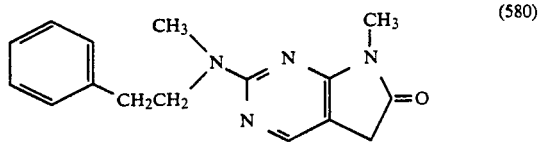 (580)
Hydrochloride of (580) (582)
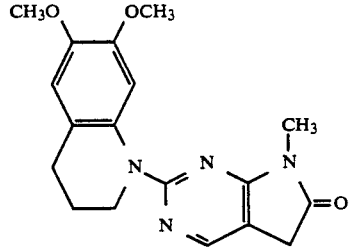 (584)
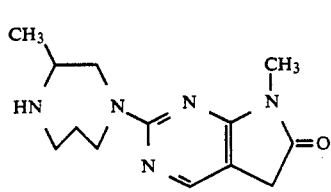 (180)

(B) Compounds of formula (I) in which —Y—Z— represents $$-CH_2-\underset{R^6}{N}-CO-:-$$

-continued (230) 

(232) 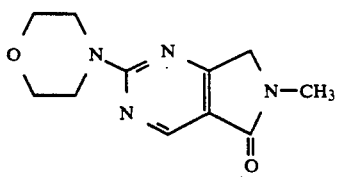

(234) 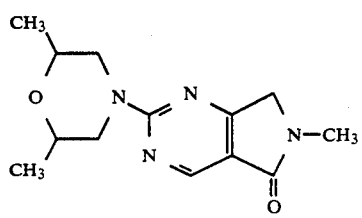

(236) 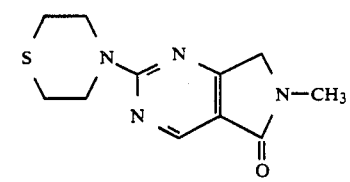

(238) 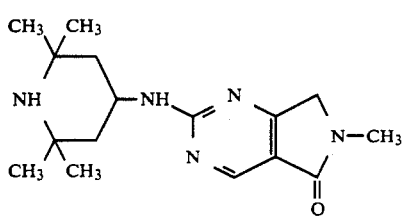

Hydrochloride of (238)  (239)

(240) 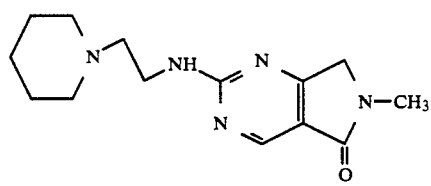

Hydrochloride of (240)  (241)

(C) Compounds of formula (I) in which Y and Z, independently from each other, represent a monovalent group:-

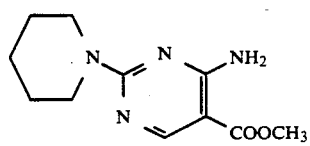

Hydrochloride of (400)  (402)

-continued (404) 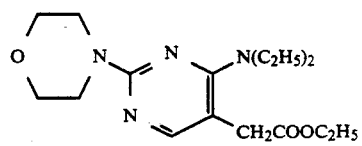

Maleate of (404)  (406)

The compounds of formula (I) provided by this invention can be produced by known processed, particularly the processes described in Japanese Laid-Open Patent Publications Nos. 140568/1986 and 87627/1986, or by treating the intermediates obtained by these processes, by a known method (for example, by reductive elimination of the protective group). Example 1 to 14 given hereinbelow describe the processes for producing the compounds of formula (I) in detail.

For example, the compounds (I) of this invention can be produced more specifically by the following processes.

(a) To produce compounds of the following formula (I)-A

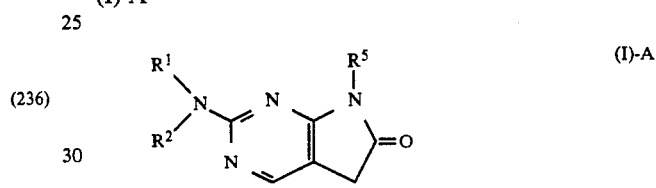

wherein $R^1$, $R^2$ and $R^5$ are as defined in formula (I), a compound of the following formula (V)

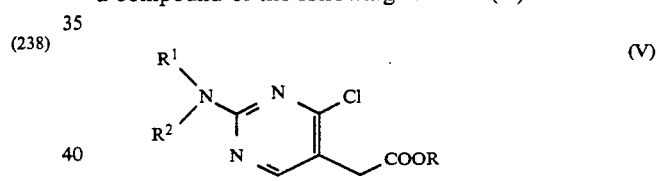

wherein $R^1$ and $R^2$ are as defined with regard to formula (I) above, and R is an alkyl group having 1 to 4 carbon atoms, is reacted with an amine of the following formula (VI)

$R^5NH_2$  (VI)

wherein $R^5$ is as defined with regard to formula (I).

This reaction beginning with the starting material can be carried out in accordance with the following Reaction Scheme 1.

Reaction Scheme 1

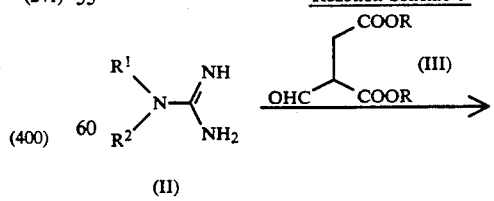

-continued
Reaction Scheme 1

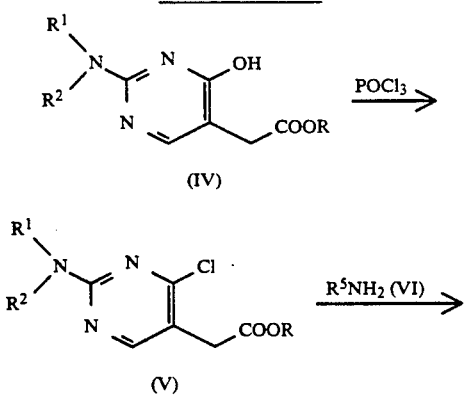

(IV)

(V)

This process can be carried out, for example, as follows. Compounds (II) and (III) are reacted at a temperature of 0° to 100° C. for 0.5 to 10 hours in a reaction medium such as water, methanol, ethanol, tetrahydrofuran or dimethylformamide to form compound (IV). Compound (IV) is reacted with phosphorus oxychloride without a solvent or in an inert solvent such as dichloroethane to form compound (V). Then, compound (V) is reacted with compound (VI) at a temperature of 80° to 150° C. in an alcohol solvent such as isopropanol and ethanol to produce compound (I)-A.

The intermediate (IV) used in Reaction Scheme 1 can also be produced in accordance with Reaction Scheme 1'.

Reaction Scheme 1'

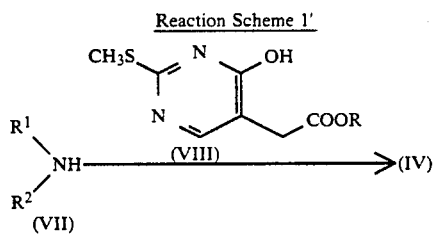

The process in Reaction Scheme 1' may be carried out by reacting compounds (VII) and (VIII) at a temperature of 100° to 200° C. in an alcohol solvent such as butanol and amyl alcohol to produce compound (IV). Compound (VIII) can also be produced by Reaction Scheme 1 except that S-methylisothiourea is used instead of compound (II).

Compounds encompassed within formula (I)-A are compounds Nos. 100, 106, 110, 114, 500, 120, 124, 128, 144, 146, 148, 150, 152, 154, 156, 158, 160, 162, 164, 166, 524, 528, 532, 536, 540, 168, 170, 174, 176, 178, 544, 548, 552, 556, 558, 560, 564, 568, 572, 575, 576, 580, 582, 180, 182, and 184.

(b) To produce compounds represented by the following formula (I)-B

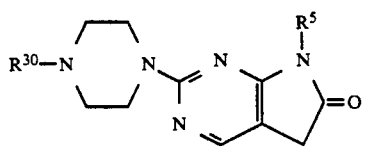

wherein $R^5$ is as defined with regard to formula (I), and $R^{30}$ represents a $C_{1-4}$ alkyl or benzoyl group, or an alkylaminocarbonyl group mono- or di-substituted by a $C_{1-6}$ alkyl group, (b¹) a compound of the following formula (IX)

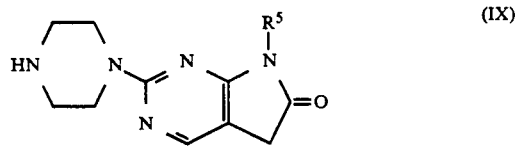

wherein $R^5$ is as defined with regard to formula (I) is reacted with a compound of the following formula (X)

$$R^{33}—Q \quad (X)$$

wherein $R^{33}$ represents a $C_{1-4}$ alkyl or benzoyl group, or a dialkylaminocarbonyl group di-substituted by an alkyl group having 1 to 6 carbon atoms, and Q represents a halogen atom, or (b²) the compound (IX) is reacted with a compound of formula (IX)

$$R^{34}—NCO \quad (XI)$$

wherein $R^{34}$ represents an alkyl group having 1 to 6 carbon atoms.

The above reaction may be shown by the following Reaction Scheme 2.

Reaction Scheme 2

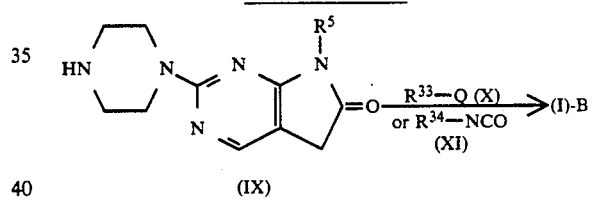

The reaction in accordance with this scheme can be carried out as follows: When a compound of formula (X) in which $R^{33}$ is an alkyl group having 1 to 4 carbon atoms is used, compounds (IX) and (X) are reacted at a temperature of 20° to 100° C. in a solvent such as ethanol in the presence of an inorganic base such as potassium carbonate to produce a compound of formula (I)-B in which $R^{30}$ is an alkyl group having 1 to 4 carbon atoms.

When a compound of formula (X) in which $R^{33}$ is a benzoyl group or a dialkylaminocarbonyl group di-substituted by an alkyl group having 1 to 6 carbon atoms is used as compound (X), compounds (IX) and (X) are reacted at a temperature of 20° to 100° C. in a basic organic solvent such as pyridine to produce a compound of formula (I)-B in which $R^{30}$ is a benzoyl group or a dialkylamino group di-substituted by an alkyl group having 1 to 6 carbon atoms.

In formula (X), Q represents chlorine, bromine or iodine.

When an isocyanate of formula (XI) is used, compounds (IX) and (XI) are reacted at a temperature of 20° to 100° C. in a solvent such as tetrahydrofuran or toluene in the presence of a basic organic compound such as triethylamine to produce a compound of formula (I)-B in which $R^{30}$ is an alkyl group.

Compounds encompassed within formula (I)-B include, for example, compounds Nos. 130, 132, 504, 508, 512, 516, 520, 136, 140 and 142.

(c) To produce compounds of the following formula (I)-C

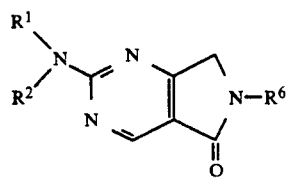
(I)-C wherein $R^1$, $R^2$ and $R^6$ are as defined with regard to formula (I), ($c^1$) a compound of formula (XII)

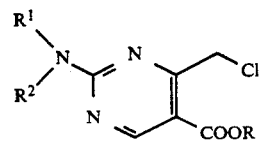
(XII)

wherein $R^1$ and $R^2$ are as defined with regard to formula (I), and R represents an alkyl group having 1 to 4 carbon atoms, is reacted with a compound of the following formula (XIII)

$R^6NH_2$          (XIII)

wherein $R^1$ is as defined with regard to formula (I), or ($c^2$) a compound of the following formula (XIV)

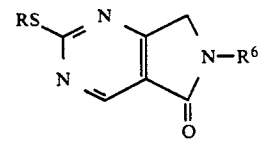
(XIV)

wherein $R^6$ is defined with regard to formula (I), and R is an alkyl group having 1 to 4 carbon atoms, is reacted with a compound of the following formula (XV)

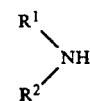
(XV)

wherein $R^1$ and $R^2$ are as defined with regard to formula (I).

The above reaction may be carried out in accordance with Reaction Scheme 3 or 4 beginning with the starting material.

Reaction Scheme 3

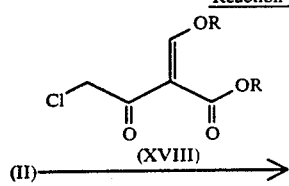

-continued
Reaction Scheme 3

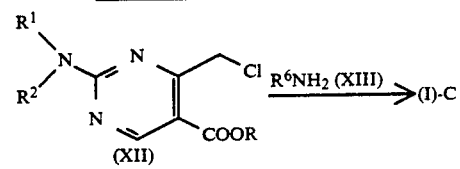

Reaction Scheme 4

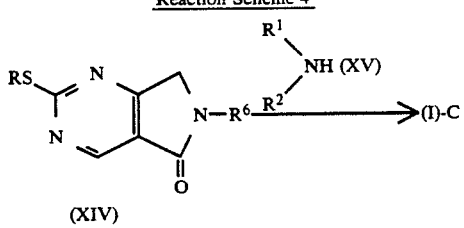

The process of Reaction Scheme 3 can be carried out, for example, as follows:

Compounds (II) and (XVIII) (in which R is an alkyl group having 1 to 4 carbon atoms) are reacted at a temperature of 0° to 100° C., preferably for 0.5 to 10 hours, in a reaction solvent such as water, methanol, ethanol, tetrahydrofuran or dimethylformamide to form compound (XII). Compound (XII) is reacted with compound (XIII) at a temperature of 0° to 150° C., preferably 0.5 to 20 hours, in a solvent such as water, an alcohol (e.g., methanol or ethanol), tetrahydrofuran, dimethylformamide, toluene or xylene to produce compound (I)-C.

The process of Reaction Scheme 4 may be carried out, for example, as follows:

Compounds (XIV) and (XV) are reacted at a temperature of 80° to 150° C. in an alcohol solvent such as butanol or amyl alcohol to form compound (I)-C. Compound (XIV) can be produced in the same way as in Reaction Scheme 3 except that S-methylisothiourea is used instead of compound (II). Compounds encompassed within formula (I)-C are compounds Nos. 200, 202, 206, 208, 210, 212, 214, 216, 218, 584, 220, 222, 224, 226, 228, 230, 232, 234, 236, 238, and 240.

(d) To produce compounds of the following formula (I)-D

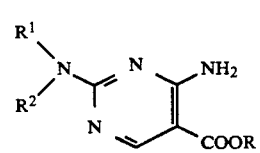
(I)-D wherein $R^1$ and $R^2$ are as defined with regard to formula (I) and R represents an alkyl group having 1 to 4 carbon atoms, a compound represented by the following formula (XVI)

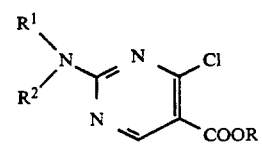
(XVI)

wherein $R^1$, $R^2$ and R are as defined above, is reacted with ammonia.

The reaction can be shown by the following Reaction Scheme 5.

Reaction Scheme 5

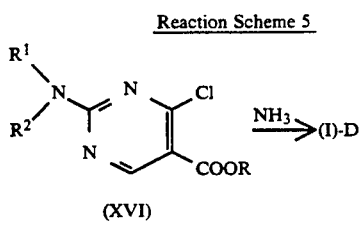

(XVI)

Reaction Scheme 5 may be carried out as follows:

Compound (XVI) can be produced by the same procedure as in the preparation of compound (V) in accordance with Reaction Scheme 1 except that a dialkyl 2-ethoxymethylenemalonate such as diethyl 2-ethoxymethylenemalonate is used instead of compound (III). The reaction of compounds (XVI) and $NH_3$ can also be carried out as in Reaction Scheme 1 to produce compound (I)-D.

An example of the compound of formula (I)-D is compound No. 400.

(e) To produce compounds of the following formula (I)-E

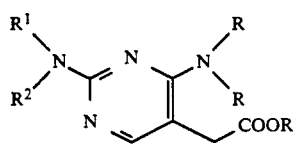

wherein $R^1$ and $R^2$ are as defined with regard to formula (I), and R's, independently from each other, represent an alkyl group having 1 to 4 carbon atoms, a compound of formula (V) is reacted with a compound of the following formula (XVII)

wherein R's, independently from each other, represent an alkyl group having 1 to 4 carbon atoms.

The above reaction may be shown by the following Reaction Scheme 6.

Reaction Scheme 6

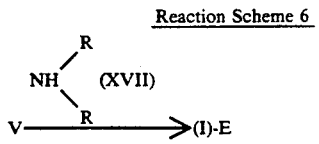

Compound (I)-E may be produced in accordance with Reaction Scheme 6 by reacting compound (VI) with compound (XVII) instead of compound (VI) in accordance with Reaction Scheme 1.

An example of the compound of formula (I)-E is compound No. 404.

The pharmaceutically acceptable salt of the compound of formula (I) may be produced in accordance with the following procedure. The hydrochloride may be produced by dissolving the corresponding compound of formula (I) in a solvent such as toluene, ether, ethanol or ethyl acetate, and blowing hydrogen chloride gas into the solution or adding concentrated hydrochloric acid to the solution. Examples of the hydrochloride are compounds Nos. 102, 114, 502, 122, 126, 129, 506, 510, 514, 518, 522, 526, 530, 534, 538, 175, 177, 546, 550, 554, 557, 562, 566, 570, 574, 578, 582, 204, 211, 215, 239, 241, 400 and 588.

Corresponding maleates and p-toluenesulfonates can be obtained in the same way by using maleic acid and p-toluenesulfonic acid instead of hydrochloric acid. Examples of such salts are maleates Nos. 104, 108, 112, 118, 138 and 404 and p-toluenesulfonate No. 542.

In accordance with this invention, the compounds of formula (I) provided by this invention have been found to be useful as therapeutic agents for neurological diseases.

The compounds of formula (1) are used normally in the form of a pharmaceutical composition, and administered through various routes, for example oral, subcutaneous, intramuscular, intravenous, intrarhinal and intrarectal routes and also by transmission through the skin.

The present invention also pertains to a pharmaceutical composition comprising a pharmaceutically acceptable carrier and a compound of general formula (I) or its pharmaceutically acceptable salt as an active ingredient. The pharmaceutically acceptable salt includes, for example, acid addition salts and quaternary ammonium (or amine) salts.

Examples of the pharmaceutically acceptable salts of the compounds (1) include salts formed from acids capable of forming pharmaceutically acceptable non-toxic acid-addition salts containing anions, such as hydrochlorides, hydrobromides, sulfates, bisulfites, phosphates, acid phosphates, acetatest maleates, fumarates, succinates, lactates, tartrates, benzoates, citrates, gluconates, glucanates, methanesulfonates, p-toluenesulfonates and naphthalenesulfonates or their hydrates, and quaternary ammonium (or amine) salts or their hydrates.

The composition of this invention may be formulated into tablets, capsules, powders, granules, troches, cachet wafer capsules, elixirs, emulsions, solutions, syrups, suspensions, aerosols, ointments, aseptic injectables, molded cataplasmas, tapes, soft and hard gelatin capsules, suppositories, and aseptic packed powders. Examples of the pharmaceutically acceptable carrier include lactose, glucose, sucrose, sorbitol, mannitol, corn starch, crystalline cellulose, gum arabic, calcium phosphate, alginates, calcium silicate, microcrystalline cellulose, polyvinyl pyrrolidone, tragacanth gum, gelatin, syrup, methyl celluloser carboxymethyl cellulose, methylhydroxybenzoic acid esters, propylhydroxybenzoic acid esters, talc, magnesium stearates, inert polymers, water and mineral oils.

Both solid and liquid compositions may contain the aforesaid fillers, binders, lubricants, wetting agents, disintegrants, emulsifying agents, suspending agents, preservatives, sweetening agents and flavoring agents. The composition of this invention may be formulated such that after administration to a patient, the active compound is released rapidly, continuously or slowly.

In the case of oral administration, the compound of formula (I) is mixed with a carrier or diluent and formed into tablets, capsules, etc. In the case of parenteral administration, the active ingredient is dissolved in a 10% aqueous solution of glucose, isotonic salt water, sterilized water or a like liquid, and enclosed in vials or ampoules for intravenous instillation or injection or intramuscular injection. Advantageously, a dissolution aid, a local anesthetic agent, a preservative and a buffer may also be included into the medium. To increase stability, it is possible to lyophilize the present composition after introduction into a vial or ampoule. Another example of parenteral administration is the administration of the pharmaceutical composition through the skin as an ointment or a cataplasm. In this case, a molded cataplasm or a tape is advantageous.

The composition of this invention contains 0.1 to 2000 mg, more generally 0.5 to 1000 mg, of the active component for each unit dosage form.

The compound of formula (I) is effective over a wide dosage range. For example, the amount of the compound administered for one day usually falls within the range of 0.003 mg/kg to 100 mg/kg. The amount of the compound to be actually administered is determined by a physician depending, for example, upon the type of the compound administered, and the age, body weight, reaction condition, etc. of the patient and the administration route.

The above dosage range, therefore, does not limit the scope of the invention. The suitable number of administrations is 1 to 6, usually 1 to 4, daily.

The compound of formula (I) by itself is an effective therapeutic agent for disorders of the peripheral nervous system and the central nervous system. If required, it may be administered in combination with at least one other equally effective drug. Examples of such an additional drug are gangliosides, mecobalamin and isaxonine.

The formulations of the compounds (I) in accordance with this invention and their biological activities will be illustrated in detail by a series of Examples B and Examples given below. It should be understood however that they do not limit the scope of the invention. Each of the following examples showing the composition of the invention uses one of the compounds described hereinabove or one of other pharmaceutically active compounds encompassed within general formula (I).

BEST MODE FOR CARRYING OUT THE INVENTION AND INDUSTRIAL APPLICABILITY

EXAMPLE 1

2-iso-Propylamino-5,6-dihydro-7-methyl-6-oxo-(7H)pyrrolo[2,3-d]pyrimidine (compound No. 100)

Phosphorus oxychloride (26.2 g) was added to 2.26 g (9.45 mmoles) of ethyl 2-isopropylamino-4-hydroxypyrimidine-5-acetate, and the mixture was heated under reflux for 3 hours. The reaction mixture was concentrated under reduced pressure, and chloroform and ice water were added. It was then neutralized with sodium hydrogen carbonate. The chloroform layer was separated, and the solvent was evaporated. The residue was purified by silica gel column chromatography to give 1.80 g (yield 74%; melting point 67°–71° C.) of ethyl 2-isopropylamino-4-chloropyrimidine-5-acetate. To the product were added 1.05 g (13.5 mmoles) of a 40% methanol solution of methylamine and 10 ml of ethanol were added, and the mixture was reacted at 120° C. for 7 hours in an autoclave. Water was added, and the mixture was extracted with chloroform. The solvent was evaporated. The residue was purified by silica gel column chromatography to give 0.50 g (yield 35%) of the desired compound.

Melting point: 120°–123° C.

$^1$H-NMR spectrum (CDCl$_3$ solution, δ ppm): 1.28(6H, d, J=5 Hz), 3.20(3H, s), 3.44 (2H, s), 4.20(1H, quint. J=5 Hz), 5.0 (1H, br.), 7.90(1H, s).

In the same way as above, the following compounds were produced.

| Compound No. | Yield (%) | Melting Point (°C.) | $^1$H-NMR spectrum (CDCl$_3$ solution, δ ppm) |
|---|---|---|---|
| 106 | 56 | 150–153 | 3.20(9H, s), 3.40(2H, s), 7.92(1H, s). |
| 110 | 71 | 190–192 | 1.9–2.1(4H, m), 3.20(3H, s), 3.40 (2H, s), 3.5–3.7(4H, m), 7.92(1H, s). |
| 114 | 65 | 120–122 | 1.68(6H, m), 3.22(3H, s), 3.44(2H, s), 3.80(4H, m), 7.92(1H, s). |
| 120 | 43 | 172.0–173.5 | 3.20(3H, s), 3.44(2H, s), 3.80(8H, s), 7.93(1H, s). |
| 124 | 37 | 181–183 (decomp.) | 2.67(4H, m), 3.20(3H, s), 3.44(2H, s), 4.16(4H, m), 7.92(1H, s). |
| 128* | 81 | 167–167 (decomp.) | 2.1–2.3(2H, m), 3.16(3H, s), 3.1–3.4 (4H, m), 3.47(2H, s), 3.8–4.2(4H, m), 7.94(1H, s). |
| 136 | 53 | 124–126 | 2.36(3H, s), 2.48(4H, t, J=5Hz), 3.20(3H, s), 3.43(2H, s), 3.86(4H, t, J=5Hz), 7.92(1H, s). |
| 500 | 55 | 95–96 | 0.96(3H, d, J=7.0Hz), 1.0–2.0(5H, m), 2.56(1H, d.d, J=10.8Hz), 2.84 (1H, m), 3.21(3H, s), 3.41(2H, s), 4.61 (2H, br.d, J=12.6Hz), 9.90(1H, s). |
| 174 | 66 | 103–105 | 0.96(3H, d, J=7.0Hz), 1.10(3H, m), 1.65(2H, m), 2.85(2H, m), 3.19(3H, s), 3.40(2H, s), 4.72(2H, br.d, J=12.6Hz), 7.90 (1H, s). |
| 175-2 | 79 | — | 0.93(3H, t, J=7Hz), 1.1–1.9(7H, m), 2.85(2H, m), 3.20(3H, S), 3.42 (2H, S), 4.75(2H, m), 7.90(1H, S). |
| 176 | 52 | 140–141 | 0.92(3H, s), 0.99(3H, s), 1.65(4H, m), 2.31(2H, d.d, J=10.5, 13.3Hz), 3.20(3H, s), 3.40(2H, s), 4.72(2H, br.d, J=12.6Hz), 7.90(1H, s). |
| 544 | 40 | 114–115 | 0.90(6H, d, J=7Hz), 1.1–3.0(10H, m), 3.19(3H, s), 3.39(2H, s), 4.80(2H, m), 7.86(1H, s). |
| 548 | 36 | 123–127 | 0.90(9H, s), 1.1–1.9(5H, m), 2.76 (2H, m), 3.21(3H, s), 3.41 (2H, s), 4.85(2H, m), 7.90(1H, s). |
| 552 | 88 | 85–90 | 1.4–2.1(4H, m), 2.6–3.4(3H, m), 3.22 (3H, s), 3.44(2H, s), 4.95(2H, br.d, J=12.6Hz), 7.27(5H, s), 7.95(1H, s). |
| 556 | 79 | 115–118 | 1.0–3.0(11H, m), 3.15(3H, s), 3.37 (2H, s), 4.72(2H, m), 7.16(5H, m), 7.84(1H, s). |
| 558 | 43 | 67–71 | 1.4–2.2(4H, m), 3.0–3.6(3H, m), 3.18 (3H, s), 3.40(2H, s), 4.50(1H, t),4.64(1H, t), 7.2–7.5(5H, m), 7.86(1H, s). |
| 560 | 71 | — | 1.94(4H, m), 2.90(1H, m), 3.20(3H, s), 3.43(2H, s), 3.5–4.3(4H, m), 7.92 (1H, s). |
| 564 | 67 | 84–87 | 1.27(3H, t, J=7Hz), 1.5–3.1(7H, m), 3.21(3H, s), 3.42(2H, s), 4.16(2H, q, J=7Hz), 4.67(2H, m), 7.91(1H, s). |
| 568 | 61 | 130–132 | 1.20–3.04(17H, m), 3.21(3H, s), 3.41 (2H, s), 4.85(2H, m), 7.91(1H, s). |
| 572 | 68 | — | 2.94(2H, t, J=7Hz), 3.25(3H, s), 3.43(2H, s), 4.08(2H, t, J=7Hz), 4.93(2H, s), 7.21(4H, m), 7.96(1H, s). |
| 576 | 34 | — | 2.85(2H, t, J=7Hz), 3.24(3H, s), 3.42(2H, s), 3.87(6H, s), 4.06(2, t, J=7Hz), 4.85(2H, s), 6.68(2H, m), 7.95(1H, s). |
| 580 | 44 | 123–125 | 2.90(2H, t, J=7Hz), 3.11(3H, s), 3.21(3H, s), 3.41(2H, s), 3.86(2H, t, J=7Hz), 7.26(5H, m), 7.93(1H, s). |
| 508 | 48 | — | 1.14(3H, t, J=7Hz), 2.53(6H, m), |

-continued

| Compound No. | Yield (%) | Melting Point (°C.) | $^1$H-NMR spectrum (CDCl$_3$ solution, δ ppm) |
|---|---|---|---|
| | | | 3.20(3H, s), 3.42(2H, s), 3.87(4H, m), 7.91(1H, s). |
| 512 | 50 | — | 1.12(6H, d, J=7Hz), 2.64(4H, m), 2.82(1H, m), 3.20(3H, s), 3.42(2H, s), 3.90(4H, m), 7.91(1H, s). |
| 516 | 90 | — | 0.8–1.7(7H, m), 2.50(6H, m), 3.21(3H, s), 3.42(2H, s), 3.85(4H, m), 7.91(1H, s). |
| 520 | 28 | — | 0.93(6H, m), 1.1–2.3(5H, m), 2.57(4H, m), 3.22(3H, s), 3.42(2H, s), 3.90(4H, m), 7.92(1H, s). |
| 524 | 54 | 106–110 | 1.0–2.5(11H, m), 2.62(4H, m), 3.20(3H, s), 3.42(2H, s), 3.83(4H, m), 7.90(1H, s). |
| 528 | 56 | 175–177 (decomp.) | 3.23(3H, s), 3.25(4H, m), 3.43(2H, s), 4.00(4H, m), 6.8–7.4(5H, m), 7.94(1H, s). |
| 532 | 88 | — | 3.24(7H, m), 3.45(2H, s), 4.02(4H, m), 6.8–7.4(4H, m), 7.95(1H, s). |
| 536 | 74 | 180–185 (decomp.) | 3.14(4H, m), 3.23(3H, s), 3.43(2H, s), 3.79(3H, s), 4.00(4H, m), 6.92(4H, m), 7.94(1H, s). |
| 540 | 9 | — | 3.22(3H, s), 3.44(6H, m), 3.98(4H, m), 6.70(2H, d, J=7Hz), 7.93(1H, s), 8.27(2H, d, J=7Hz). |
| 586 | 40 | — | 1.08(6H, d, J=7Hz), 2.60(4H, m), 2.70(1H, m), 3.38(3H, s), 3.44(2H, s), 3.6–4.1(8H, m), 7.92(1H, s). |

*NMR was measured in DMSO-d$^6$ solution (same hereinafter).

EXAMPLE 2

Ethyl 2-morpholino-4-diethylaminopyrimidine-5-acetate (compound No. 404)

Phosphorus oxychloride (11.7 ml) was added to 3.35 g (12.5 mmoles) of ethyl 2-morpholino-4-hydroxypyrimidine-5-acetate, and the mixture was heated under reflux for 4 hours. The reaction mixture was concentrated under reduced pressure, and methylene chloride and ice water were added. It was neutralized with sodium hydrogen carbonate. The methylene chloride layer was dried over anhydrous sodium sulfate, and concentrated under reduced pressure. To the product were added 15 ml of ethanol and 7.0 g (95.7 mmoles) of diethylamine, and in an autoclave, the mixture was reacted at 120 ° C. for 7 hours. Water was added, and the mixture was extracted with methylene chloride. The solvent was evaporated, and the residue was purified by silica gel column chromatography to give 2.8 g (yield 56%) of the desired compound as an oil.

$^1$H-NMR spectrum (CDCl$_3$ solution, δ ppm):
1.16(6H, t, J=7 Hz), 1.24(3H, t, J=7 Hz), 3.20(4H, q, J=7 Hz), 3.44(2H, s), 3.74 (8H, s), 4.16(2H, q, J=7 Hz), 7.80(1H, s).

EXAMPLE 3

2-Butylaminocarbonylpiperazino-5,6-dihydro-7-methyl-6-oxo(7H) pyrrolo[2,3-d]pyrimidine (compound No. 130)

THF (30 ml), 1 ml of triethylamine and 0.43 g (4.34 mmoles) of n-butyl isocyanate were added to 0.5 g (2.14 mmoles) of 2-piperazino-5,6-dihydro-7-methyl-6-oxo(7H)pyrrolo[2,3-d]pyrimidine, and the mixture was stirred at room temperature for 3 hours. It was concentrated under reduced pressure, and after addition of water, extracted with chloroform. The chloroform layer was concentrated under reduced pressure, and the residue purified by silica gel column chromatography to give 0.15 g (yield 21%) of the desired product.

Melting point: 168°–178 ° C. (decomp.).

$^1$H-NMR spectrum (CDCl$_1$ solution, δ ppm):
0.95(3H, t, J=7 Hz), 1.45(4H, m), 3.20 (3H, s), 3.24(2H, s), 3.50(4H, m), 3.85 (4H, m) , 4.44 (1H, m) , 7.92 (1H, s).

EXAMPLE 4

2-Diethylaminocarbonylpiperazino-5,6-dihydro-7-methyl-oxo(7H) pyrrolo[2,3-d]pyrimidine (compound No. 132)

Pyrimidine (15 ml) and 0.35 g (2.6 mmoles) of diethylaminocarbamoyl chloride were added to 0.6 g (2.6 moles) of 2-piperazino-5,6-dihydro-7-methyl-6-oxo(7H) pyrrolo[2,3d-]-pyrimidine, and the mixture was reacted at 70° C. for 2 hours. The reaction mixture was concentrated under reduced pressure, and after addition of an aqueous solution of sodium hydrogen carbonate, extracted with chloroform. The chloroform layer was concentrated under reduced pressure. The residue was purified by silica gel chromatography to give 0.24 g (yield 28%) of the desired product.

Melting point: 84.5°–86.0° C.

$^1$H-NMR spectrum (CDCl$_3$ solution, δ ppm):
1.16(6H, t, J=7 Hz), 3.22(3H, s), 3.29 (8H, m), 3.44(2H, s), 3.84(4H, m), 7.93 (1H, s).

EXAMPLE 5

2-Benzoylpiperazino-5,6-dihydro-7-methyl-6-oxo(7H) pyrrolo[2,3-d]pyrimidine (compound No. 504)

One gram of triethylamine, 50 ml of methylene chloride and 0.6 g (4.3 mmoles) of benzoyl chloride were added to 1.0 g (4.3 mmoles) of 2-piperazino-5,6-dihydro-7-methyl-6-oxo(7H) pyrrolo[2,3-d]pyrimidine, and the mixture was reacted overnight at room temperature. The reaction mixture was concentrated under reduced pressure, and after adding an aqueous solution of sodium hydrogen carbonate, extracted with chloroform. The chloroform layer was concentrated under reduced pressure, and the residue was purified by silica gel column chromatography to give 1.1 g (yield 76%) of the desired compound.

Melting point: 158°–160° C.

$^1$H-NMR spectrum (CDCl$_1$ solution, δ ppm):
3.19(3H, s), 3.43(2H, s), 3.80(8H, m), 7.43 (5H, m) , 7.90 (1H, s).

EXAMPLE 6

2-Methylthio-5,6-dihydro-7-methyl-6-oxo(7H)-pyrrolo[2,3-d]pyrimidine (compound No. 134)

Phosphorus oxychloride (59.0 g) was added to 4.84 g (21.2 mmoles) of ethyl 2-methylthio-4-hydroxy-pyrimidine-5-acetate, and the mixture was heated under reflux for 3 hours. The reaction mixture was concentrated under reduced pressure, and after adding chloroform, neutralized with an aqueous solution of sodium hydrogen carbonate. The chloroform layer was concentrated under reduced pressure. To the concentrate were added 20 ml of ethanol and 3.48 g (44.9 mmoles) of a 40 methanol solution of methylamine, and the mixture was reacted at 100 ° C. for 5 hours in an autoclave. The solvent was evaporated under reduced pressure, and after adding water, the mixture was extracted with chloroform. The chloroform layer was concentrated under reduced pressure, treated with activated carbon in ethanol, and recrystallized to give 1.50 g (yield 36%) of the desired compound.

Melting point: 183°–185 °C. (decomp.)

$^1$H-NMR spectrum (CDCl$_3$ solution, δ ppm):
2.60(3H, s), 3.28(3H, s), 2.54(2H, s), 8.14(1H, s).

EXAMPLE 7

2-iso-Propylamino-5,6-dihydro-7-methyl-6-oxo-(7H)pyrrolo[2,3-d]pyrimidine hydrochloride (compound No. 102)

0.49 g (2.4 mmoles) of 2-isopropylamino-5,6-dihydro-7-methyl-6-oxo(7H)pyrrolo[2,3-d]pyrimidine was dissolved in 30 ml of toluene, and hydrogen chloride gas was blown into the solution. The solution was concentrated under reduced pressure, and then washed with hexane to give 0.53 g (yield 92%) of the desired compound.

Melting point: 272°–275° C.

$^1$H-NMR spectrum (CDCl$_3$ solution, δ ppm):
1.38(6H, d, J=5 Hz), 3.30(3H, s), 3.60 (2H, br.s), 4.30(1H, br.), 7.90(1H, br.), 8.90(1H, br.).

Similarly, compounds tabulated below were produced.

| Compound No. | Yield (%) | Melting Point (°C.) | $^1$H-NMR spectrum (CDCl$_3$ solution, δ ppm) |
|---|---|---|---|
| 116 | 93 | 203–205 (decomp.) | 1.79(6H, br.s), 3.31(3H, s), 3.62(2H, s), 4.04(4H, br.s), 8.04(1H, br.s). |
| 122 | 100 | 215–253 | 3.27(3H, s), 3.64(2H, s), 3.84(4H, m), 4.10(4H, m), 8.06(1H, s). |
| 126 | 91 | 239–241 (decomp.) | 2.84(4H, m), 3.28(3H, s), 3.65(2H, s), 4.38(4H, m), 8.12(1H, s). |
| 129* | 91 | | 2.1–2.3(2H, m), 3.20(3H, s), 3.2–3.4(4H, m), 3.66(2H, s), 3.9–4.1(2H, m), 4.1–4.3 (2H, m), 8.02(1H, s). |
| 502 | 100 | deliquescent 213–214 | 1.10(3H, br.s), 1.80(5H, m), 2.4–3.4 (2H, m), 3.30(3H, s), 3.60(2H, s), 4.76(1H, br. d, J=12.6Hz), 8.08(1H, s). |
| 175 | 40 | deliquescent 186–190 | 1.0(3H, d. J=7.0Hz), 2.0–2.1(5H, m), 2.9–3.5(2H, m), 3.25(3H, s), 3.59 (2H, s), 4.85(2H, br.d, J=12.6Hz), 8.05(1H, br.s). |
| 175-4 | 73 | 208–211 | 0.93(3H, t, J=7Hz), 1.1–2.2(7H, m), 3.14(2H, m), 3.28(3H, S), 3.58 (2H, S), 4.90(2H, m), 8.02(1H, S). |
| 177 | 100 | 238–240 | 1.05(6H, m), 1.4–2.1(4H, m), 2.2–2.9 (2H, m), 3.28(3H, s), 3.61(2H, s), 4.90(2H, br.d, J=12.6Hz) 8.06(1H, s). |
| 546 | 88 | 240–242 (decomp.) | 0.90(6H, d, J=7Hz), 1.0–2.2(7H, m), 2.8–3.7(8H, m), 4.92(2H, m), 8.0(1H, s). |
| 550 | 82 | 234–236 (deomp.) | 0.90(9H, s), 1.35(3H, m), 1.94(2H, m), 3.10(2H, m), 3.27(3H, s), 3.58 (2H, s), 5.00(2H, m), 8.05(1H, s). |
| 554 | 90 | 138–140 | 1.5–2.4(4H, m), 2.6–3.5(3H, m), 3.28 (3H, s), 3.61(2H, s), 5.10(2H, br.d, J=12.6Hz), 7.25(5H, m), 8.10(1H, s). |
| 557 | 83 | 212–215 (decomp.) | 1.1–3.2(11H, m), 3.24(3H, s), 3.59 (2H, s), 4.90(2H, m), 7.20(5H, m), 8.03(1H, s). |
| 562 | 90 | 173–175 (decomp.) | (CDCl$_3$-CD$_3$OD) 2.10(4H, m), 3.12(1H, m), 3.30(3H, s), 3.65(2H, s), 4.14(4H, m), 7.94(1H, s). |
| 566 | 85 | 196–198 (decomp.) | 1.30(3H, t. J=7Hz), 1.6–2.9(5H, m), 3.30(3H, s), 3.49(2H, s), 3.65(2H, m), 4.18(2H, q, J=7Hz), 4.70(2H, m), 8.10(1H, s). (1H, br.s) |
| 570 | 71 | 270–275 (decomp.) | 1.60–3.06(13H, m), 3.22(3H, s), 3.48 (2H, m), 3.52(4H, m), 5.03(2H, m), 7.94(1H, s). |
| 574 | 82 | 231–237 (decomp.) | 3.10(2H, m), 3.33(3H, s), 3.63(2H, s), 4.24(2H, m), 5.10(2H, m), 7.26(4H, m), 8.13(1H, s). |
| 578 | 82 | 223–227 (decomp.) | 3.0(2H, m), 3.35(3H, s), 3.65(2H, s), 3.91(6H, s), 4.04(2H, m), 4.98(2H, s), 6.80(2H, m), 8.10(1H, s). |
| 582 | 95 | 255–258 | (CDCl$_3$-CD$_3$OD) 3.03(2H, t, J=7Hz), 3.27(3H, s), 3.32(3H, s), 3.64(2H, s), 4.07(2H, t, J=7Hz), 7.29(5H, m), 7.95(1H, s). |
| 510 | 82 | >300 | (CDCl$_3$-CD$_3$OD) 1.47(3H, t, J=7Hz), 3.0–3.8(13H, m), 4.92(2H, m), 7.98(1H, s). |
| 514 | 85 | 291–293 (decomp.) | (CDCl$_3$-CD$_3$OD) 1.48(6H, d, J=7Hz), 2.8–4.0(12H, m), 4.92(2H, m), 7.95(1H, s). |
| 518 | 87 | 293–294 (decomp.) | (CDCl$_3$-CD$_3$OD) 0.99(3H, t, J=7Hz), 1.2–2.1(4H, m), 3.06(4H, m), 3.23(3H, s), 3.52 (2H, s), 3.68(2H, m), 4.88(2H, m), 7.94(1H, s). |
| 522 | 91 | 235–240 (decomp.) | 0.9–2.3(11H,m), 3.0(2H, m), 3.22(3H, s), 3.46(4H,m), 4.0(2H,m), 4.88 (2H, m), 7.94(1H, s). |
| 526 | 80 | 260–265 (decomp.) | 1.1–3.1(13H, m), 3.20(3H, s), 3.46 (2H, s), 3.94(4H, m), 4.83(2H, m), 7.93(1H, s). |
| 530 | 86 | 247–252 (decomp.) | (CDCl$_3$-CD$_3$OD) 3.30(3H, s), 3.43(4H, m), 3.63(2H, s), 4.20(4H, m), 6.9–7.5 (5H, m), 7.96(1H, s). |
| 534 | 86 | 131–136 (decomp.) | (CDCl$_3$-CD$_3$OD) 3.32(3H, s), 3.44(4H, m), 3.66(2H, s), 4.24(4H, m), 6.9–7.4 (4H, m), 7.95(1H, s). |
| 538 | 90 | 263–265 | (CDCl$_3$-CD$_3$OD) 3.28(3H, s), 3.42(4H, m), 3.58(2H, s), 3.84(3H, m), 4.34(4H, m), 6.96 (2H, m), 7.36(2H, m), 7.98(1H, s). |
| 506 | 86 | 273–275 (decomp.) | (CDCl$_3$-CD$_3$OD) 3.29(3H, s), 3.64(2H, s), 3.84(4H, m), 4.08(4H, m), 7.47(5H, m), 7.95(1H, s). |
| 559 | 95 | 106–110 | 1.4–2.3(4H, m), 3.0–3.8(3H, m), 3.22 (3H, s), 3.58 (2H, s), 4.3–4.8(br. 2H), 7.1–74.(5H, m), 7.99(1H, s). |
| 588 | 90 | >300 | (CDCl$_3$-CD$_3$OD) 1.48(6H, d, J=7Hz), 2.8–4.2(18H, m), 9.96(1H, s). |
| 211* | 100 | 151–153 | 0.88(3H, t, J=7Hz), 1.52(2H, m), 2.98(3H, s), 3.22(2H, m), 4.34(2H, s), 8.50(1H s). |
| 239 | 100 | >300 | 1.46(6H, s), 1.48(6H, s), 1.70(8H, m), 2.99(3H, s), 4.33(3H, br.s), 8.08(2H, m), 8.56(1H, s). |
| 241 | 100 | 278–281 | 1.70(6H, s), 3.0(3H, s), 3.25(6H, m), 3.75(2H, s), 4.35(2H, s), 8.10 (1H, m), 8.59(1H, s). |

*$^1$H-NMR was measured in DMSO-d$^6$ solution.

EXAMPLE 8

2-iso-Propylamino-5,6-dihydro-7-methyl-6-oxo-(7H) pyrrolo[2,3-d]pyrimidine maleate (compound No. 104)

6.37 g (30.9 mmoles) of 2-isopropylamino-5,6-dihydro-7-methyl-6-oxo(7H)pyrrolo[2,3-d]pyrimidine was dissolved in 50 ml of ethyl acetate, and 3.58 g (30.8 mmoles) of maleic acid was added. The mixture was stirred at room temperature for 1 hour. The resulting crystals were collected by filtration to give 8.90 g (yield 90%) of the desired compound.

Melting point: 158°–160° C.

$^1$H-NMR spectrum (CDCl$_3$ solution, δ ppm):

1.24(6H, d, J-6 Hz), 3.12(3H, s), 3.50
(2H, s), 3.9-4.2(1H, m), 6.20(2H, s),
7.90(1H, a).

Similarly, compounds tabulated below were produced.

| Compound No. | Yield (%) | Melting Point (°C.) | $^1$H-NMR spectrum (CDCl$_3$ solution, δ ppm) |
|---|---|---|---|
| 108 | 89 | 155-162 (decomp.) | 3.20(3H, s), 3.26(6H, s),3.50 (2H, s), 6.20(2H, s), 7.94(1H, s). |
| 112** | 79 | 128-130 | 2.0-2.2(4H, m), 3.22(3H, s), 3.56 (2H, br.s), 3.6-3.8(4H, m), 6.24(4H, s), 7.90(1H, s). |
| 118 | 69 | 135-137 | 1.64(6H, br.s), 3.12(3H, s), 3.46 (2H, s), 3.7-3.9(4H, m), 6.22(2H, s), 7.90(1H, s). |
| 138 | 98 | 178-179 (decomp.) | 2.88(3H, s),3.16(3H, s), 3.2-3.3(4H, m), 3.48(2H, s), 4.0-4.2(4H, m), 6.18(2H, s), 7.96(1H, s). |
| 175-1 | 75 | 95-97 | 1.0(3H, d, J-7Hz), 1.1-2.3(5H, m), 3.14(2H, m), 3.26(3H, S), 3.56 (2H, S), 4.64(2H, s), 6.52(2H, S), 8.2(1H, S). |
| 175-3 | 71 | 98-99 | 0.93(3H, t, J=7Hz), 1.1-2.1(7H, m), 3.14 2H, m), 3.26(3H, S), 3.56 (2H, S), 4.64(2H, s), 6.32(2H, S), 8.16(1H, S). |
| 175-5 | 72 | 104-109 | (CDCl$_3$-CD$_3$OD) 0.93(3H, t, J=7Hz), 1.1-1.96(7H, m), 2.88(2H, m), 3.22(3H, S), 3.44 (2H, S), 4.70(2H, m), 6.82(2H, S), 7.88(1H, S). |
| 406 | 56 | oil | 1.28(6H, t, J=7Hz), 1.30(3H, t, J=7Hz), 3.54(2H, s), 3.60(4H, q, J=7Hz), 3.80(8H, s),4.22(2H, q, J=7Hz),6.32(2H, s), 7.89(1H, s), 10.91(2H, br.s). |
| 302 | 70 | 207-208 | 2.9-3.0(4H, m), 3.11(3H, s), 3.93(2H, s), 4.1-4.3(4H, m), 6.20(2H, s), 7.39(5H, s), 8.75(1H, s). |

**dimaleate

EXAMPLE 9

2-(4-Pyridylpiperazino)-5,6-dihydro-7-methyl-6-oxo(7H) pyrrolo[2,3-d]pyrimidine p-toluenesulfonate (compound No. 542)

A solution of p-toluenesulfonic acid (0.1 g; 0.6 mmole) in 5 ml of chloroform-methanol was dissolved in a solution of 0.18 g (0.6 mmole) of 2-(4-pyridylpiperazino)-5,6-dihydro-7-methyl-6-oxo(7H) pyrrolo[2,3-d]-pyrimidine in 30 ml of chloroform-methanol, and the mixed solution was stirred at room temperature for 1 hour. The solvent was evaporated under reduced pressure. The precipitated crystals were washed with hexane to give 0.25 g (yield 90%) of the desired compound.

Melting point: 195°-200° C.

$^1$H-NMR spectrum (CDCl$_3$—CD$_3$OD solution, δ ppm):
2.37(3H, s), 3.23(3H, s), 3.49(2H, s),
3.7-4.2 (8H, m) , 7.06 (2H, d, J=7 Hz),
7.20(2H, d, J=7 Hz), 7.76(2H, d, J=7 Hz),
7.96(1H, s), 8.16(2H, d, J=7 Hz).

EXAMPLE 10

2-iso-Propylamino-S-oxo-6-methyl-5,6-dihydro-(7H) pyrrolo[3,4-d]pyrimidine (compound No. 202)

A solution composed of 2.2 g (32 mmoles) of iso-propylamine, 5.18 g (37 mmoles) of s-methylisothiourea sulfate and 20 ml of water was stirred at room temperature for 24 hours. Water was evaporated under reduced pressure. To the residue were added 7.8 g (35 mmoles) of ethyl 4-chloro-2-ethoxymethyleneacetoacetate and 30 ml of methanol and further 1.4 g of sodium hydroxide. The mixture was stirred for 2 hours, and then 27 g (348 mmoles) of a 40% methanol solution of methylamine was added dropwise. After the addition, the mixture was further stirred for 2 hours. The precipitated crystals were collected by filtration, and extracted with water and chloroform. The chloroform layer was dried over anhydrous magnesium sulfate. The solvent was evaporated under reduced pressure to give 0.8 g (yield 12%) of the desired compound.

Melting point: 201°-202 ° C.

$^1$H-NMR spectrum (CDCl$_3$ solution, δ ppm):
1.27(6H, d, J=7 Hz), 3.12(3H, s), 4.20
(2H, s), 4.27(1H, m), 5.50(1H, br.s),
8.63(1H, s).

EXAMPLE 11

2-Morpholino-6-methyl-5-oxo-5,6-dihydro(7H) pyrrolo[3,4-d]pyrimidine (compound No. 232)

79 g (320 mmoles) of 4-chloromethyl-5-ethoxycarbonyl-2-methylthiopyrimidine was dissolved in 300 ml of methanol, and 50 g (640 mmoles) of a 40% methanol solution of methylamine was added dropwise over 15 minutes, and the mixture was stirred for 15 hours. The product was separated by filtration and dried to give 11 g (yield 18%) of 2-methylthio-6-methyl-5-oxo-5,6-dihydro(7H) pyrrolo[3,4-d]pyrimidine. The resulting product (1.5 g; 7.7 mmoles) and 3.4 g (38.5 mmoles) of morpholine were dissolved in 20 ml of n-amyl alcohol, and the solution was heated under reflux for 7 hours. The reaction mixture was cooled, and the precipitated crystals were separated by filtration to give 0.75 g (yield 42%) of the desired compounds.

Melting point: 184°-187° C. (decomp.)

$^1$H-NMR spectrum (CDCl$_3$ solution, δ ppm):
3.16(3H, s), 3.85(8H, m), 4.24(2H, s),
8.68(1H, s).

By the same way, the following compounds were prepared.

| Compound No. | Yield (%) | Melting point (°C.) | $^1$H-NMR spectrum (CDCl$_3$ solution, δppm) |
|---|---|---|---|
| 214 | 36 | 149-151.3 | 1.00(6H, d, J=7Hz), 1.93(1H, m), 3.14(3H, s), 3.34(2H, t, J=7Hz), 4.23(2H, s), 8.62(1H, s). |
| 216 | 64 | 204-205.5 | 2.03(4H, m), 3.03(3H, s), 3.65 (4H, m), 4.23(2H, s), 8.67(1H, s). |
| 218 | 37 | 175.5-177 | 1.64(6H, m), 3.14(3H, s), 3.87 (4H, m), 4.19(2H, s), 8.64(1H, s). |
| 226 | 28 | 133.5-135.5 | 1.67(8H, m), 3.12(3H, s), 3.82(4H, t, J=7Hz), 4.20(2H, s), 8.65(1H, s). |
| 236 | 55 | 169-170 | 2.96(4H, m), 3.15(3H, s), 4.24 (2H, s), 4.26(4H, m), 8.67(1H, s). |
| 210 | 51 | — | 1.00(3H, t, J=7Hz), 1.66(2H, sex, J=7Hz), 3.15(3H, s), 3.46(2H, q, J=7Hz), 4.24(2H, s), 8.64(1H, s). |
| 584 | 63 | 114-116 | 0.98(6H, d, J=7Hz), 1.4-1.9(4H, m), 2.40(4H, t, J=12.6Hz), 3.13(3H, s), 4.20(2H, s), 4.86(2H, br.d, J=12.6Hz), 8.64(1H, s). |
| 234 | 57 | 221-222 | 1.25(3H, s), 1.32(3H, s), 2.67(2H, d.d, J=10.8, 14.2Hz), 3.14(3H, s), 3.65(2H, m), 4.22(2H, s), 4.70(2H, d.d., J=10.8, 1.5Hz), 8.68(1H, s). |
| 238 | 29 | 139-140 | 1.01(2H, d.d, J=12.3, 12.3Hz), 1.18 (6H, s), 1.32(6H, s), 2.04(2H, d.d, J=12.3, 3.6Hz), 3.15(3H, s), 4.24 (2H, s), 4.40(1H, m), 5.36(1H, br.d, |

| Compound No. | Yield (%) | Melting point (°C.) | $^1$H-NMR spectrum (CDCl$_3$ solution, δppm) |
|---|---|---|---|
| | | | J=7.2Hz), 8.65(1H, s). |
| 240 | 46 | 131-132 | 1.52(6H, m), 2.44(4H, m), 2.56(2H, t, J=7.2, 5.4Hz), 4.23(2H, s), 6.27(1H, m), 8.66(1H, 2). |

EXAMPLE 12

Methyl 2-piperidino-4-aminopyrimidine-5-carboxylate (compound No. 400)

Ethylene dichloride (50 ml) and 10 ml of phosphorus oxychloride were added to 5.6 g (23.6 mmoles) of methyl 2-piperidino-4-hydroxypyrimidine-5-carboxylate, and the mixture was heated under reflux for 5.5 hours. The reaction mixture was concentrated under reduced pressure, and after adding chloroform and water, neutralized with sodium hydrogen carbonate. The chloroform layer was separated and the solvent was evaporated. To the residue were added 70 ml of THF and 27.8 g of 25% ammonium hydroxide. The mixture was reacted at 70° C. for 1.5 hours in an autoclave. The reaction mixture was is concentrated under reduced pressure and recrystallized from toluene/hexane to give 5.0 g (yield 90%) of the desired compound.

$^1$H-NMR spectrum (CDCl$_3$ solution, δ ppm)
1.62(6H, m), 3.82(3H, s), 3.80(4H, m), 8.60(1H, s).

EXAMPLE 13

N-methyl-2-(4-benzylpiperazino)-4,5-pyrimidinedicarboxylic acid imide (compound No. 300)

Potassium hydroxide (8.4 g; 150 mmoles), 50 ml of ethanol and 10 ml of water were added to 19.9 g (50 mmoles) of diethyl 2-(4-benzylpiperazino)-4,5-pyrimidinedicarboxylate, and the mixture was stirred for 1 hour at room temperature and then for 2 hours at 40° C. Hydrochloric acid was added to the solution to adjust its pH to 3. The resulting crystals were separated by filtration, and washed with ethyl acetate. The crystals (18.1 g) were dissolved in 527 ml of methylene chloride, and 21.3 g (211 mmoles) of triethylamine and 12.5 g (105 mmoles) of thionyl chloride were added. The mixture was stirred at room temperature for 1 hour, and then cooled to −78° C. 8.17 g (105 mmoles) of a 40% methanol solution of methylamine was added, and the temperature was raised to room temperature. The mixture was stirred at this temperature for 1 hour. The reaction mixture was concentrated under reduced pressure, and the resulting solid was washed with water. To 14.4 g of the solid were added 3.32 g (40.4 mmoles) of sodium acetate and 41.3 g (404 mmoles) of acetic anhydride were added. The mixture was heated under reflux for 2 hours. The reaction mixture was concentrated under reduced pressure, and after adding water, the mixture was stirred for 30 minutes. The resulting solid was purified by silica gel column chromatography to give 9.72 g (yield 56%) of the desired compound.

Melting point: 158.5°-159.8° C.

$^1$H-NMR spectrum (CDCl$_3$ solution, δ ppm):
2.56(4H, t, J=4 Hz), 3.18(3H, s), 3.58 (2H, s), 4.06(4H, m), 7.36(5H, s), 8.72 (1H, s).

EXAMPLE 14

2-iso-Propylamino-5-oxo-6-methyl-5,6-dihydro(7H) pyrrolo[3,4-d]pyrimidine hydrochloride (compound No. 204)

Concentrated hydrochloric acid (0.27 g; 2.7 mmoles) was added to a solution of 0.56 g (2.7 mmoles) of 2-iso-propylamino-5-oxo-6-methyl-5,6-dihydro(7H) pyrrolo-3,4-d]pyrimidine in 6 ml of chloroform, and the solution was stirred for 30 minutes. The solvent was then evaporated under reduced pressure, and the residue was washed with ether to give 0.6 g (yield 92%) of the desired compound.

Melting point: 176°-183° C. (decomp.)

Similarly, the following compounds were produced.

| Compound No. | Yield (%) | Melting point (°C.) | $^1$H-NMR spectrum (CDCl$_3$ solution, δppm) |
|---|---|---|---|
| 215 | 100 | 167-168 | 0.94(6H, d, J=7Hz), 1.86(1H, m) 2.97(3H, s), 3.20(2H, m), 3.37 (2H, s), 8.57(1H, s). |
| 402 | 100 | <300 | 1.62(6H, br.s), 3.80(7H, br.s), 8.30(1H, s). |

EXAMPLE 1B

Tablets each containing 10 mg of an active ingredient were prepared by the following procedure.

| | Per tablet |
|---|---|
| Active ingredient | 10 mg |
| Corn starch | 55 mg |
| Crystalline cellulose | 35 mg |
| Polyvinyl pyrrolidone (as 10% aqueous solution) | 5 mg |
| Carboxymethyl cellulose calcium | 10 mg |
| Magnesium stearate | 4 mg |
| Talc | 1 mg |
| Total | 120 mg |

The active ingredient, corn starch and crystalline cellulose were passed through an 80-mesh sieve and thoroughly mixed. The mixed powder was granulated together with the polyvinyl pyrrolidone solution, and passed through an 18-mesh sieve. The resulting granules were dried at 50° to 60° C. and again passed through an 18-mesh sieve to adjust their sizes. The carboxymethyl cellulose calcium, magnesium stearate and talc, which had been passed through an 80-mesh sieve, were added to the granules. They were mixed and tableted by a tableting machine to produce tablets each having a weight of 120 mg.

EXAMPLE 2B

Tablets each containing 200 mg of an active ingredient were produced by the following procedure.

| | Per tablet |
|---|---|
| Active ingredient | 200 mg |
| Corn starch | 50 mg |
| Crystalline cellulose | 42 mg |
| Silicic anhydride | 7 mg |
| Magnesium stearate | 1 mg |
| Total | 300 mg |

The above components were passed through an 80-mesh sieve and thoroughly mixed. The resulting mixed powder was compression-molded to produce tablets each having a weight of 300 mg.

EXAMPLE 3B

Capsules each containing 100 mg of an active ingredient were produced by the following procedure.

|  | Per capsule |
| --- | --- |
| Acive ingredient | 100 mg |
| Corn starch | 40 mg |
| Lactose | 5 mg |
| Magnesium stearate | 5 mg |
| Total | 150 mg |

The above components were mixed, passed through an 80-mesh sieve, and thoroughly mixed. The resulting mixed powder was filled into capsules in an amount of 150 mg for each.

EXAMPLE 4B

Injectable preparations in vials each containing 5 mg of an active ingredient were produced by the following procedure.

|  | Per vial |
| --- | --- |
| Active ingredient | 5 mg |
| Mannitol | 50 mg |

Just prior to use; these compounds were dissolved in 1 ml of distilled water for injection, and administered.

EXAMPLE 5B

Injectable preparations in ampoules each containing 50 mg of an active ingredients were produced in accordance with the following recipe.

|  | Per ampoule |
| --- | --- |
| Active ingredient | 50 mg |
| Sodium chloride | 18 mg |
| Distilled water for injection | proper amount |
| Total | 2 ml |

EXAMPLE 6B

An adhesive patch containing 17.5 mg of an active ingredient was produced by the following procedure.

Ten parts of poly(ammonium acrylate) was dissolved in 60 parts of water. Two parts of glycerin diglycidyl ether was dissolved under heat in 10 parts of water. Furthermore, 10 parts of polyethylene glycol (grade 400), 10 parts of water and 1 part of an active ingredient were stirred to form a solution. While the aqueous solution of poly(ammonium acrylate) was stirred, the aqueous solution of glycerin diglycidiyl ether and the solution containing the active ingredient, polyethylene glycol and water were added and mixed. The resulting solution for hydrogel was coated on a pliable plastic film so that the rate of the active ingredient was 0.5 mg per cm. The surface was covered with releasing paper and cut to a size of 35 $cm^2$ to form an adhesive patch.

EXAMPLE 7B

An adhesive patch containing 10 mg of an active ingredient was produced by the following procedure.

An aqueous sol is prepared from 100 parts of poly(sodium acrylate), 100 parts of glycerin, 150 parts of water, 0.2 part of triepoxypropyl isocyanurate, 100 parts of ethanol, 25 parts of isopropyl myristate, 25 parts of propylene glycol and 15 parts of the active ingredient. The sol was then coated to a thickness of 100 micrometers on the non-woven fabric surface of a composite film composed of a rayon non-woven fabric and a polyethylene film to form an adhesive layer containing the drug. The amount of the release aids (isopropyl myristate and propylene glycol) contained in this layer was about 30% by weight. The adhesive layer was then crosslinked at 25° C. for 24 hours, and a releasing film was bonded to the adhesive layer surface. The entire film was then cut into pieces each having an area of 35 cm.

The biological activities in vitro of the compounds of formula (I) on cells of the nervous system were tested. The cells tested were mouse neuroblastoma cell line neuro-2a (Dainippon Pharmaceutical Co., Ltd.) which have been established as the cells of the nervous system. The above nerve cells were grown in an incubator at 37° C. in the presence of 5% carbon dioxide gas exponentially, and then cultivated for a certain period of time together with the compounds of formula (I). The results demonstrate that the compounds of formula (I) have nerve cell growth promoting activity and neurite formation and sprouting promoting activity which are markedly higher with a significance than a control, and are equal to, or higher than, isaxonine as a control drug (the compound described in Japanese Patent Publication No. 28548/1984).

The biological activities of the compounds of formula (I) in accordance with this invention on rat PC-12 pheochromocytoma cell line were also tested. When NGF is added to PC-12 cells, the neurites sprout. It was shown that when the compound (I) of this invention is added at this time, the binding of NGF to the PC-12 cells and the up-take of NGF into the cells increased.

When the effect of the compounds (I) of this invention on the binding of NGF to rabbit superior cervical ganglion was examined, they were found to promote the NGF binding.

Rats whose sciatic nerves were crushed were prepared as a model of peripheral nervous disorder, and the effects of the compounds of this invention on it were tested. It was made clear that the compounds (I) of the present invention have an effect of promoting recovery of the interdigit distance and the weight of the soleus muscle to normal values.

Rat and mouse models of central nervous disorders were prepared, and the pharmacological effects of the compounds (I) of this invention were tested. Specifically, nigral dopamine cells of the rat brain were chemically destroyed by injecting a very small amount of 6-hydroxydopamine to induce motor imbalance. Two weeks later, dopamine cells of fetal brain were transplanted in the caudate nucleus into the lesioned side of the rat brain and an attempt was made to improve the motor trouble. Specifically, beginning on the day of transplantation, the compound (I) of the invention was intraperitoneally administered every day over 2 weeks, and the activity of the compounds (I) of the invention on the improvement of the motor imbalance and the growth of the transplanted cells was examined. It was found that the compounds (I) of the invention have a promoting effect on the improvement of the motor trouble.

Rats and mice having a nerve trouble by mercury poisoning were prepared and the activity of the compounds (I) of the invention was tested. The compounds (I) were found to have a promoting effect on the improvement of the condition and recovery to a normal condition, a curative effect on chemicals-induced disorders and an effect of improving and recovering learning and memory.

Thus, it has been made clear that the compounds (I) of this invention are useful as agents for improving or curing various neurological diseases of mammals, such as troubles in peripheral and central nerves, and also as agents for improving learning and memory.

Various types of neuropathy including, for example, various peripheral nerve disorders accompanied by motorgenic, sensory or objective flex retardation, and alcohol-induced or drug-induced, diabetic and metabolic, or idiopathic peripheral nerve disorders, including traumatic, inflammatory or immunological nerve root lesions may be cited as such neurological diseases. More specific examples include facial palsy, sciatic nerve paralysis, spinal muscular atrophy, muscular dystrophy, myasthenia gravis, multiple sclerosis, amyotrophic lateral sclerosis, acute disseminated cerebromyelitis, Guillan-Barre syndrome, postvaccinal encephalomyelitis, SMON disease, dementia, Alzheimer syndrome, a condition after cranial injury, cerebral ischemia, sequela of cerebral infarction of cerebral hemorrhage, and rheumatism. These examples are not limitative.

By a toxicity test, the compounds of this invention were found to have only weak toxicity and side effects, and be used as safe and highly useful medicines.

Experimental Example 1

The effects of the compounds of this invention on neuroblastoma cells were examined by the following method. Mouse neuro 2a cells in the logarithmic growth period in the Dulbeccols modified Eagle's medium ID-MEM, containing 100 units/ml of penicillin G sodium and 100 micrograms/ml of streptomycin sulfate) containing 10% of FCS were seeded in a 48-well plate so that the number of cells was 1,000 cells/well, and cultured for one day in 0.25 ml of the culture fluid in each well in an incubator containing 5% of carbon dioxide gas in air at 37 °C. Then, a 4% aqueous glutaraldehyde solution in the same amount as a medium (0.25 ml) was added, and the culture fluid was left to stand at room temperature for 2 hours to fix the cells. After washing with water, a 0.05% aqueous solution of methylene blue was added to stain the cells. Under a microscope, the number of cells containing outgrown neurites (cells having at least one neurite with a length of at least two times as large as the long diameter of the cell) was counted visually, and the proportion of these cells in the entire cells was calculated. The well was observed over 5 or more visual fields (at least 2% of the entire surface area of the well) continuous to the left and right from a mark put at the center of the well, and more than 200 cells was counted. One drug compound was used in 6 different concentrations at most, and three runs were conducted for each concentrations. The results were expressed as a mean ±S.D., and the results are shown in Table 1.

Mouse neuroblastoma cells NS-20Y were similarly cultured in a dish coated with polyornithine, and the effects of the compounds were examined. The results obtained after 24 hours and 48 hours from the start of culturing are shown in Table 2.

TABLE 1

| Run No. | Compound | Action on neuro-2-a cells Number of cells having neurites with a length at least two times the diameter of cells/total number of cells, % (concentration of the compound) |
|---|---|---|
| 1 | 402 | 29.6 ± 5.5(3 mM), 25.9 ± 3.6(10 mM), 24.6 ± 6.3(1 mM), 18.9 ± 2.5(20 mM), 11.9 ± 5.0(0.3 mM), 5.3 ± 0.8(0.1 mM). |
|  | isaxonine | 10.9 ± 1.7(3 mM). |
|  | control | 1.9 ± 0.9 |
| 2 | 128 | 39.4 ± 1.9(1 mM), 16.2 ± 2.5(0.3 mM), 6.4 ± 1.5(0.1 mM). |
|  | 302 | 10.1 ± 0.9(3 mM), 4.0 ± 2.6(0.3 mM). |
|  | 112 | 20.9 ± 1.3(3 mM), 10.2 ± 1.6(1 mM), 4.7 ± 0.4(0.3 mM). |
|  | isaxonine | 32.7 ± 1.7(10 mM). |
|  | control | 1.8 ± 0.9 |
| 3 | 102 | 30.5 ± 0.3(3 mM), 15.1 ± 2.0(1 mM), 5.3 ± 1.3(0.3 mM). |
|  | isaxonine | 28.5 ± 3.0(10 mM). |
|  | control | 2.5 ± 0.7 |
| 4 | 204 | 22.8 ± 1.1(10 mM), 20.1 ± 5.1(5 mM), 9.4 ± 1.7(3 mM). |
|  | control | 2.0 ± 0.7 |
| 5 | 104 | 28.4 ± 1.4(3 mM), 12.3 ± 3.3(1 mM), 7.2 ± 0.7(0.3 mM), 4.6 ± 0.7(0.03 mM). |
|  | 138 | 24.6 ± 3.3(1 mM), 23.0 ± 3.2(0.3 mM), 13.3 ± 2.1(0.1 mM), 7.1 ± 1.5(0.03 mM). |
|  | 118 | 21.0 ± 1.8(1 mM), 7.6 ± 1.0(0.3 mM), 4.8 ± 0.3(0.03 mM). |
|  | 108 | 14.4 ± 1.3(3 mM), 5.7 ± 1.1(1 mM), 3.9 ± 1.6(0.1 mM), 3.0 ± 1.0(0.03 mM). |
|  | 130 | 7.6 ± 2.8(0.3 mM), 6.9 ± 1.9(0.1 mM), 6.4 ± 1.7(1 mM), 5.1 ± 0.2(0.03 mM). |
|  | 132 | 12.0 ± 2.0(1 mM), 7.1 ± 1.6(0.3 mM), 4.3 ± 0.4(0.03 mM). |
|  | isaxonine | 32.7 ± 4.4(10 mM), 8.0 ± 1.5(20 mM), 8.0 ± 1.2(3 mM). |
|  | control | 1.8 ± 0.8 |
| 6 | 122 | 15.7 ± 1.3(3 mM), 4.4 ± 1.1(0.1 mM), 4.0 ± 1.2(1 mM). |
|  | 406 | 12.9 ± 3.7(1 mM), 10.4 ± 1.0(0.3 mM), 5.2 ± 1.7(0.03 mM). |
|  | 216 | 6.7 ± 0.9(3 mM), 6.5 ± 3.3(10 mM). |
|  | 226 | 8.1 ± 3.4(1 mM), 4.6 ± 0.9(0.3 mM). |
|  | 126 | 24.7 ± 0.7(10 mM), 14.9 ± 0.9(3 mM), 9.2 ± 1.7(1 mM). |
|  | 218 | 9.9 ± 2.2(3 mM), 5.0 ± 1.3(1 mM), |
|  | isaxonine | 32.9 ± 3.5(10 mM), 7.6 ± 2.7(3 mM). |
|  | control | 2.8 ± 0.4 |
| 7 | 502 | 4.1 ± 0.6(0.1 mM), 7.5 ± 0.2(0.2 mM), 11.0 ± 4.8(0.3 mM), 20.7 ± 2.8(0.5 mM). |
|  | 175 | 4.2 ± 0.8(0.1 mM), 11.7 ± 1.3(0.2 mM), 21.0 ± 1.4(0.3 mM), 15.7 ± 1.7(0.5 mM). |
|  | 554 | 7.3 ± 0.9(0.1 mM), 30.7 ± 1.0(0.2 mM), 34.0 ± 2.9(0.3 mM), 22.0 ± 6.1(0.5 mM). |
|  | isaxonine | 27.8 ± 1.1(10 mM). |
|  | control | 2.5 ± 0.1 |
| 8 | 177 | 5.0 ± 3.0(0.1 mM), 15.7 ± 4.9(0.2 mM), 27.2 ± 1.5(0.3 mM), 16.3 ± 1.8(0.5 mM). |
|  | 514 | 13.0 ± 3.0(0.3 mM), 16.2 ± 2.3(0.5 mM), 28.2 ± 6.9(1 mM), 16.5 ± 1.5(2 mM). |
|  | isaxonine | 2.2 ± 3.1(5 mM). |
|  | control | 1.7 ± 0.3 |
| 9 | 550 | 3.1 ± 1.0(0.01 mM), 3.6 ± 1.4(0.03 mM), 36.1 ± 0.4(0.1 mM), 14.3 ± 5.9(0.3 mM). |
|  | 562 | 5.2 ± 1.5(0.3 mM), 5.8 ± 1.7(1 mM), 10.2 ± 2.6(3 mM), 12.5 ± 0.4(10 mM). |
|  | isaxonine | 30.2 ± 3.5(10 mM). |
|  | control | 2.6 ± 1.0 |
| 10 | 522 | 3.7 ± 1.6(0.03 mM), 4.1 ± 0.9(0.1 mM), 9.5 ± 3.2(0.3 mM), 24.7 ± 3.6(1 mM). |
|  | isaxonine | 26.7 ± 3.3(10 mM). |
|  | control | 2.4 ± 1.6 |

TABLE 1-continued

Action on neuro-2-a cells

| Run No. | Compound | Number of cells having neurites with a length at least two times the diameter of cells/total number of cells, % (concentration of the compound) |
|---|---|---|
| 11 | 566 | 7.5 ± 3.0(0.3 mM), 5.4 ± 2.6(1 mM). |
|  | isaxonine | 15.7 ± 4.2(3 mM). |
|  | control | 1.2 ± 1.1 |
| 12 | 534 | 6.4 ± 2.2(0.01 mM), 6.5 ± 0.7(0.03 mM). |
|  | 538 | 9.1 ± 0.9(0.3 mM), 10.5 ± 2.5(1 mM). |
|  | isaxonine | 26.7 ± 7.7(10 mM). |
|  | control | 1.8 ± 0.8 |
| 13 | 574 | 12.1 ± 0.6(0.3 mM), 11.6 ± 3.3(1 mM). |
|  | 578 | 6.3 ± 1.7(0.03 mM), 6.6 ± 3.0(0.1 mM). |
|  | isaxonine | 26.7 ± 7.7(10 mM). |
|  | control | 1.8 ± 0.8 |
| 14 | 582 | 7.9 ± 0.8(0.1 mM), 9.8 ± 2.0(0.3 mM), 24.1 ± 8.6(1 mM), 12.8 ± 2.8(3 mM). |
|  | isaxonine | 30.8 ± 2.9(10 mM). |
|  | control | 3.2 ± 1.6 |
| 15 | 526 | 6.2 ± 0.4(0.1 mM), 14.9 ± 0.7(0.3 mM). |
|  | 570 | 10.6 ± 1.9(0.03 mM), 17.1 ± 0.6(0.1 mM), 29.4 ± 6.8(0.3 mM), 8.7 ± 0.8(1 mM). |
|  | isaxonine | 30.7 ± 5.9(10 mM). |
|  | control | 2.9 ± 1.9 |
| 16 | 506 | 2.5 ± 1.6(0.01 mM), 4.8 ± 0.5(0.03 mM), 4.2 ± 1.7(0.1 mM), 6.2 ± 1.6(0.3 mM). |
|  | isaxonine | 15.8 ± 2.2(3 mM). |
|  | control | 2.9 ± 1.0 |
| 17 | 546 | 6.4 ± 1.0(0.03 mM), 16.3 ± 1.2(0.1 mM), 26.9 ± 4.8(0.3 mM), 46.3 ± 5.5(1 mM). |
|  | 557 | 4.3 ± 1.7(0.03 mM), 25.6 ± 3.9(0.1 mM). |
|  | isaxonine | 17.4 ± 4.2(3 mM), 23.3 ± 2.2 (10 mM). |
|  | control | 2.3 ± 0.6 |
| 18 | 215 | 5.8 ± 0.3(0.3 mM), 14.5 ± 2.4(3 mM). |
|  | 232 | 5.3 ± 3.1(1 mM), 8.9 ± 0.5(3 mM). |
|  | 236 | 4.2 ± 0.6(0.3 mM), 6.2 ± 0.5(1 mM). |
|  | 234 | 5.5 ± 1.7(3 mM), 8.9 ± 0.9(10 mM). |
|  | 239 | 3.4 ± 1.6(0.03 mM), 3.4 ± 0.9(0.1 mM). |
|  | isaxonine | 22.1 ± 2.1(10 mM), 10.5 ± 4.9(3 mM). |
|  | control | 2.4 ± 0.2 |
| 19 | 175 | 6.1 ± 1.0(0.1 mM), 27.9 ± 4.4(0.3 mM). |
|  | isaxonine | 27.0 ± 3.8(10 mM). |
|  | control | 3.3 ± 0.4 |
| 20 | 502 | 6.9 ± 1.7(0.1 mM), 12.2 ± 2.0(0.3 mM). |
|  | isaxonine | 25.6 ± 6.2(10 mM). |
|  | control | 2.2 ± 0.5 |
| 21 | 542 | 6.2 ± 1.3(0.01 mM). |
|  | 530 | 6.6 ± 0.4(0.3 mM), 7.5 ± 1.2(1 mM). |
|  | isaxonine | 27.4 ± 2.4(10 mM). |
|  | control | 1.8 ± 1.3 |
| 22 | 588 | 11.3 ± 2.6(0.01 mM), 9.3 ± 1.9(0.1 mM). |
|  | isaxonine | 20.6 ± 1.9(10 mM). |
|  | control | 2.1 ± 0.2 |
| 23 | 211 | 5.4 ± 0.7(0.1 mM), 5.3 ± 0.2(1 mM), 19.0 ± 2.9(3 mM). |
|  | 584 | 4.4 ± 1.8(0.03 mM), 4.2 ± 0.6(0.3 mM). |
|  | 510 | 8.2 ± 1.6(0.1 mM), 11.4 ± 1.4(0.3 mM). |
|  | 241 | 5.6 ± 2.7(0.3 mM), 10.0 ± 0.7(1 mM). |
|  | 177 | 4.9 ± 2.4(0.03 mM), 6.1 ± 0.1(0.1 mM), 14.2 ± 1.1(0.3 mM), 28.4 ± 4.5(1 mM). |
|  | 554 | 4.6 ± 2.7(0.03 mM), 9.6 ± 2.7(0.1 mM), 20.2 ± 2.23(0.3 mM), 3.58 ± 9.8(1 mM). |
|  | isaxonine | 21.0 ± 1.4(10 mM), 9.6 ± 1.7(3 mM). |
|  | control | 3.3 ± 0.4 |
| 24 | 559 | 9.2 ± 0.8(0.1 mM). |
|  | isaxonine | 19.4 ± 3.1(10 mM). |
|  | control | 2.4 ± 0.9 |

TABLE 2

Activity on NS-20Y cells

| Compound | Number of cells in which neurites appeared/total number of cells (concentration of the compound) | |
|---|---|---|
| 138 | 2/51(0.5 mM) | 27/49(1.0 mM) |
|  | 1/52(0.3 mM) | 3/51(0.3 mM) |
| control | 1/54 | 3/50 |
| 118 | 35/50(1.0 mM) | 25/50(1.0 mM) |
|  | 4/52(0.5 mM) | 9/49(0.5 mM) |
| control | 1/56 | 1/52 |
| 122 | 4/54(1.0 mM) | 10/52(0.5 mM) |
|  | 1/52(0.5 mM) | 8/52(0.3 mM) |
| control | 1/54 | 2/51 |
| 132 | 5/52(1.0 mM) | 26/54(1.0 mM) |
|  | 0/51(0.5 mM) | 8/51(0.5 mM) |
| control | 0/50 | 3/54 |
| 218 | 2/52(0.5 mM) | 20/53(1.0 mM) |
|  | 2/50(0.3 mM) | 4/50(0.5 mM) |
| control | 1/51 | 2/50 |
| 177 | 7/55(0.5 mM) | 12/50(0.1 mM) |
|  | 1.50(0.25 mM) | 4/50(0.25 mM) |
| control | 2/48 | 4/50 |
| 550 | 3/57(0.25 mM) | 8/50(0.1 mM) |
|  | 2/52(0.1 mM) | 7/50(0.25 mM) |
| control | 0/50 | 3/50 |
| 510 | 11/50(0.25 mM) | 16/51(0.5 mM) |
|  | 9/52(0.1 mM) | 9/50(0.25 mM) |
| control | 0/50 | 1/45 |
| 554 | 6/54(0.25 mM) | 9/50(0.25 mM) |
|  | 9/50(0.1 mM) | 7/50(0.1 mM) |
| control | 1/53 | 3/50 |
| 175 | 10/54(0.5 mM) | 8/53(0.25 mM) |
|  | 6/50(0.25 mM) | 4/50(0.1 mM) |
| control | 1/55 | 3/50 |
| 502 | 6/50(1.0 mM) | 12/50(1.0 mM) |
|  | 2/54(0.5 mM) | 8/50(0.3 mM) |
| control | 1/50 | 1/50 |
| 562 | 8/48(0.5 mM) | 4/51(0.1 mM) |
|  | 8/56(0.1 mM) | 4/50(0.25 mM) |
| control | 3/51 | 2/50 |
| 566 | 19/54(0.5 mM) | 4/53(0.1 mM) |
|  | 3/50(0.25 mM) | 1/50(0.25 mM) |
| control | 2/50 | 0/50 |
| 514 | 7/50(0.5 mM) | 8/51(0.5 mM) |
|  | 6/50(1.0 mM) | 3/54(0.3 mM) |
| control | 1/50 | 2/50 |
| 518 | 7/50(1.0 mM) | 10/50(1.0 mM) |
|  | 6/57(0.3 mM) | 7/50(0.3 mM) |
| control | 2/50 | 1/51 |
| 218 | 2/52(0.5 mM) | 20/53(1.0 mM) |
|  | 2/50(0.3 mM) | 4/50(0.5 mM) |
| control | 1/51 | 2/50 |
| 177 | 7/55(0.5 mM) | 12/50(0.1 mM) |
|  | 1/50(0.25 mM) | 4/50(0.25 mM) |
| control | 2/48 | 4/50 |
| 550 | 3/57(0.25 mM) | 8/50(0.1 mM) |
|  | 2/52(0.1 mM) | 7/50(0.25 mM) |
| control | 0/50 | 3/50 |
| 510 | 11/50(0.25 mM) | 16/51(0.5 mM) |
|  | 9/52(0.1 mM) | 9/50(0.25 mM) |
| control | 0/50 | 1/45 |
| 554 | 6/54(0.25 mM) | 9/50(0.25 mM) |
|  | 0/50(0.1 mM) | 7/50(0.1 mM) |
| control | 1/53 | 3/50 |
| 175 | 10/54(0.5 mM) | 8/53(0.25 mM) |
|  | 6/50(0.25 mM) | 4/50(0.1 mM) |
| control | 1/55 | 3/50 |
| 546 | 53/58(0.1 mM) | 13/48(0.1 mM) |
|  | 10/52(0.05 mM) | 3/50(0.05 mM) |
| control | 0/50 | 0/50 |
| 557 | 5/52(0.05 mM) | 4/50(0.05 mM) |
| control | 0/50 | 1/50 |
| 502 | 6/50(1.0 mM) | 12/50(1.0 mM) |
|  | 2/54(0.5 mM) | 8/50(0.3 mM) |
| control | 1/50 | 1/50 |
| 562 | 8/48(0.5 mM) | 4/51(0.1 mM) |
|  | 8/56(0.1 mM) | 4/50(0.25 mM) |
| control | 3/51 | 2/50 |

Experimental Example 2

Curative Effect on Rats with Crushed Sciatic Nerves

The curing effect of the compound (I) of the invention was tested on rats having crushed sciatic nerves as a model of peripheral nervous disorder using (1) a change in the action of the hind paw with the crushed sciatic nerves and (2) a change in the weight of the muscle as an index of the course of degeneration and regeneration of peripheral nerves.

In the experiment, male Wistar rats (6 weeks old), seven per group, were used. The sciatic nerves were crushed by a method similar to the method of Yamatsu et al. (see Kiyomi Yamatsu, Takenori Kaneko, Akifumi Kitahara and Isao Ohkawa, Journal of Japanese Pharmacological Society, 72, 259–268 (1976) and the method of Hasegawa et al. (see Kazoo Hasegawa, Naoji Mikuni and Yutaka Sakai, Journal of Japanese Pharmacological Society, 74, 721–734 (1978). Specifically, under anesthesia with pentobarbital (40 mg/kg, i.p.), the left side sciatic nerve was exposed at the femur and that site of the exposed sciatic nerve which was 5 mm to the center from the branched part between the N. tibialis and the N. suralis was crushed using a modified artery, klomme, having a width of 2 mm and a gap of 0.1 mm. After the operation, the rats were assigned to the test groups at random.

Compound No. 118 was selected as the compound (I) of the invention and intraperitoneally administered to the rats once a day from the day of operation to the 22nd day. A group to which mecobalamin (made by Gedeon Richter Ltd.) was administered and a group to which 0.9 % saline was administered were used as controls. The following items were measured with the lapse of time (on the 1st, 4th, 7th, 10th, 14th, 17th, 21st, and 23rd days after the crushing of the sciatic nerves).

(1) Change in the action of the side of the hind paw with the crushed sciatic nerve The distance between digits was measured because this is a good index which functionally shows the degeneration and regeneration of the nerve and its change can be measured with the lapse of time.

By a method similar to the method of Hasegawa [Hasegawa, K., Experientia, 34, 750–751 (1978)], the distance between the first and fifth digits of the hind paw was measured.

The ratio of the measured distance to the normal distance was calculated and expressed in percentage (%). The average calculated values and the standard errors (S. E.) are shown in Table 3. To the values of the test groups which are significantly different, by the t-test of Student, from that of the control group to which physiological saline was administered, superscript is attached where $p<0.05$ and superscript **, where $p<0.01$.

The distance between the digits was about half (50%) of the normal distance immediately after the crushing of the sciatic nerve, and tended to decline until the tenth day. No significant difference was seen among the groups. Regeneration proceeded in the drug-administered groups on the 14th and 17th days, but they showed no significant difference from the group to which saline was administered. On the 21st day, there was an apparent tendency to quicker recovery in the drug-administered groups and the mecobbalamin-administered group, and these groups also show significant differences from the group to which saline was administered. Recovery continued also on the 23rd day.

(2) Change in the weight of muscle

It is known that removal of a nerve or its disorder causes atrophy of the muscle which is under its control, and the atrophy is gradually cured by re-control by the nerve. For this reason, a change in the weight of the muscle, which is quantitative, was selected as an Index. Twenty-three days after the operation, the soleus muscles of both sides of paws were extracted under anesthesia with pentobarbital, and their weights were measured. The ratio of the weight of the soleus muscle on the crushed side to that of normal side was calculated and expressed in percentage (b). The average values and the standard errors (S. E.) of the groups are shown in Table 3.

TABLE 3

| | | Curative effect with rats crushed in the sciatic nerve | | |
|---|---|---|---|---|
| Drug | Dose (mg/kg, i.p.) | Rate of recovery of the interdigit distance (%) | | Rate of recovery in muscle weight (%) |
| | | 21st day | 23rd day | 23rd day |
| Saline | 1 ml/kg | 62.0 ± 2.4 | 71.1 ± 3.4 | 51.8 ± 1.2 |
| Compound 118 | 30 | 79.8 ± 2.5*** | 87.9 ± 3.3** | 59.6 ± 2.8* |
| Mecobalamin | 0.5 | 79.1 ± 2.6*** | 88.3 ± 4.0** | 55.0 ± 3.5 |

Comparison with the saline-administered group by the Student t-test
*P < 0.05,  < P: 0.01, *P < 0.001
Rats used: Seven per group

Experimental Example 3

Promoting effect on the improvement of motor imbalance due to injury of the rat's brain cells by transplantation of fetal cerebral cells Nigral dopaminergic nerve cells at the left side of the brain of 4-week old female Wistar rats (body weight 100 g) were lesioned by injecting a very small quantity of 6-hydroxydopamine. The rats showed a tendency to rotate spontaneously in a direction opposite to the lesioned side for several days, but no apparent abnormal action was observed after that. Upon administration of methamphethamine (5 mg/kg, i.p.) to the rats having the lesioned nigral dopaminergic nerve cells, they began rotational movement toward the lesioned side.

After two weeks from the destruction by the administration of the drug, portions of the truncus corporis callosi containing dopamine cells (i.e., substantia nigra and the tagmentum at the abdomen side) were cut from the brain of a fetal rat of 14 to 17 days of age, cut finely, and treated with trypsin. Then, the extracted tissues were incubated at 370° C. for 30 minutes, and the tissues were subjected to pipetting to form a suspension. Five microliters of the suspension was transplanted each into two sites of the caudate nucleus of the lesioned side (10 microliters in total, about 105cells).

Each of the compounds (I) in a dose of 100 mg/kg (i.p.) was administered every day over two weeks from the day of transplantation. The rotational movements induced by administration of methamphetamine were examined 2 weeks and 1 week before, and 2 weeks and 4 weeks after, the transplantation and the administration of the drug. The number of rotational movements within one minute was counted at intervals of 10 minutes after the administration of methamphetamine, and the total number of rotational movements counted six times was averaged to find a mean number of the rotational movements.

The results are shown in Table 4.

TABLE 4

Effect of the drug on the methamphetamine-induced rotational movement of rats

Number of rotational movements of rats and average values thereof (mean ± S.D.)
Number of weeks after transplantation of nigral dopamine cells

| | Compound | −2W | −1W | 2W | 4W | 6W |
|---|---|---|---|---|---|---|
| Run No. 1 | 104 | 12.3 ± 3.7 | 10.8 ± 3.8 | 2.0 ± 3.2 | 0.1 ± 0.6 | 0 ± 0 |
| | Saline | 11.0 ± 4.1 | 12.0 ± 6.0 | 3.7 ± 4.7 | 0.4 ± 1.1 | 0.4 ± 2.0 |
| Run No. 2 | 104 | 10.1 ± 6.1 | 10.4 ± 5.2 | 3.1 ± 3.8 | 0.25 ± 1.1 | 1.75 ± 3.0 |
| | 118 | 9.1 ± 5.6 | 10.8 ± 4.9 | 1.9 ± 3.2 | 0.7 ± 1.5 | 0.4 ± 1.1 |
| | Saline | 11.2 ± 4.1 | 11.2 ± 6.2 | 3.7 ± 5.6 | 1.5 ± 3.3 | 2.7 ± 6.4 |
| | | −2W | −1W | 3W | 4W | 6W |
| Run No. 3 | 118 | — | 13.9 ± 7.4 | *5.5 ± 7.2 | −0.1 ± 1.8 | −0.6 ± 2.8 |
| | 554 | — | 14.6 ± 7.6 | *7.0 ± 6.0 | 3.1 ± 3.0 | 0.3 ± 2.3 |
| | Saline | — | 16.7 ± 9.1 | *11.2 ± 9.6 | 5.3 ± 8.3 | 2.8 ± 5.4 |

Rats used: Five to six per group
*Data at 2 W.

Experimental Example 4

Improvement of learning and memory of mice with nerve disorder induced by mercury poisoning, and recovery effect Male BalbC strain mice, 7 weeks old, were first caused to learn a T-shaped maze three times in a week so that they run straight from a starting point to a safety area. Then, methylmercury chloride (MMC for short) was administered orally in a dose of 6 mg/kg/day for 6 days. A group of mice to which saline was administered in a dose of 0.1 ml/10 g/day was used as a control group. Beginning with the day next to the day of administering KMC, compounds Nos. 102 and 116 were intraperitoneally administered over 10 days in a dose of 69.5 mg/kg/day and 76.9 mg/kg/day, respectively, so as to make the mole numbers of the compounds equal. On the sixth day after administration of the drug (namely, on the 12th day after start of the experiment), learning of the T-shaped maze was resumed, and the running behaviors of the mice were observed. The number of mice which could be experimented in the T-shaped maze on the 10th and 11th days after the resumption (21st and 22nd days after the start of the experiment) was counted and expressed as a denominator. The number of mice which ran to the safety area within 5 seconds at least 8 times out of ten trial runnings was counted and expressed as a numerator. The decrease in the number of the test animals was due to death by MMC poisoning. The time (seconds) required for the animals to run to the safety area was measured, and the mean±standard error (SE) was calculated. The results are shown in Table 5.

The results demonstrate the effect of the compounds of the invention to improve learning and memory of the mouse and their recovery effect.

TABLE 5

Improvement of the learning and memory of mice with induced nerve disorder and the recovery effect Number of mice which ran to the safety area within 5 seconds and the running time (seconds)

| Treatment | 10th day | | 11th day | |
|---|---|---|---|---|
| Saline 0.1 ml/10 g/day | 5/6 | 3.0 ± 0.6 | 5/6 | 2.3 ± 0.3 |
| MMC | 4/7 | 2.5 ± 0.4 | 5/7 | 2.1 ± 0.4 |
| MMC + 102 69.5 mg/kg · ip/day | 6/6 | 2.1 ± 0.2 | 6/6 | 3.0 ± 0.6 |
| MMC + 116 76.9 mg/kg · ip/day | 7/7 | 2.1 ± 0.3 | 7/7 | 2.0 ± 0.3 |

Experimental Example 5

The acute toxicity of the compounds of the invention was examined by the following method.

Male ddy-strain 5-week old mice and male Wistar-strain 8 week old rats, five per group, were used as experimental animals. Each of the compounds was dissolved in saline and administered perorally (p.o.) or intraperitoneally (i.p.), and the toxicity of the compound was assessed 24 hours after the administration. The results are shown in Tables 6 and 7.

TABLE 6

Acute toxicity (LD$_{50}$) in mouse

| | Number of dead animals/ number of animals tested Dose (mg/kg, p.o.) | | Estimated LD$_{50}$ |
|---|---|---|---|
| Compound | 550 | 1000 | (mg/kg, p.o.) |
| 402 | 0/5 | 3/5 | >1000 |
| 128 | 0/5 | 0/5 | >1000 |
| 112 | — | 0/5 | >1000 |
| 102 | — | 0/5 | >1000 |
| 138 | — | 0/5 | >1000 |
| 118 | — | 0/5 | >1000 |
| 108 | — | 2/5 | >1000 |
| 122 | — | 1/5 | >1000 |
| 406 | — | 0/5 | >1000 |
| 216 | 0/5 | — | >550 |
| 218 | 0/5 | — | >550 |
| 126 | — | 0/5 | >1000 |
| 132 | — | 1/5 | >1000 |

—: Not tested

TABLE 7

| Acute toxicity ($LD_{50}$) in mouse | |
|---|---|
| Compound | Estimated $LD_{50}$ (mg/kg, i.p.) |
| 138 | 250–500 |
| 118 | 500–1000 |
| 117 | 250–500 |
| 514 | 125–250 |
| 554 | 250–500 |
| 175 | 500–1000 |
| 570 | <125 |
| 550 | <500 |
| 562 | 500–1000 |
| 546 | 500–1000 |
| 557 | 500–1000 |
| 559 | 500–1000 |
| 566 | 500–1000 |
| 574 | 500–1000 |
| 578 | 500–1000 |
| 582 | 500–1000 |
| 502 | 500–1000 |
| 506 | 500–1000 |
| 522 | >500 |
| 538 | >500 |
| 534 | >500 |
| 518 | >250 |
| 510 | >250 |

The compounds of general formula (I) provided by this invention have a promoting effect on the proliferation of nerve cells and the formation and sprouting of neurites and a nerve regenerating effect and a motor function recovering effect in rats and mice having nerve disorders, and can be used suitably for improving and curing neurological diseases such as disorders of peripheral nerves or central nerves and dementia. They are expected to be used also suitably for the recovery, improving and curing of neurological diseases caused by nervous tissues and cells which have to do with perceptive and sensory functions and an autonomic function.

It has been found that the compounds (I) of the invention have biological activities equal to, or higher than, those of isaxonine and mecobalamin as a control as shown in Experimental Examples 1 to 4 and Tables 1 to 5. The toxicity of the compounds (1) of this invention are generally weak as shown in Experimental Example 5 and Tables 6 and 7. Thus, the compounds (I) of this invention are generally considered to be highly active and highly safe drugs and very useful with weak toxicity.

We claim:

1. A pyrimidine compound represented by the following formula (I)

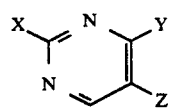 (I)

wherein X represents
(i) a group of the following formula (I)-1

 (I)-1 wherein $R^1$ represents a hydrogen atom or an alkyl group having 1 to 4 carbon atoms, $R^2$ represents a cyclohexyl, phenyl, benzyl or piperidyl group which may be substituted by $C_{1-4}$ alkyl group, or an alkyl group having 1 to 4 carbon atoms which may be substituted by a piperidino group or $R^1$ and $R^2$ together with the nitrogen atom to which they are bonded form a heterocyclic ring selected from the group consisting of

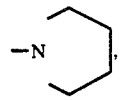 (a)

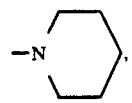 (b)

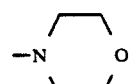 (c)

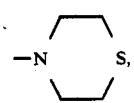 (d)

and

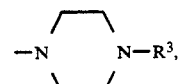 (e)

wherein $R^3$ represents an alkylaminocarbonyl group mono- or di-substituted by a $C_{1-6}$ alkyl group, and the heterocyclic group may optionally be mono- to penta-substituted by a $C_{1-4}$ alkyl group, or substituted by a $C_{3-5}$ polymethylene group on the adjoining ring-member carbons, or (ii) a group represented by the following formula (I)-2

$$-S-R^4 \qquad (I)\text{-}2$$

wherein $R^4$ represents an alkyl group having 1 to 4 carbon atoms, Y represents an amino group or a substituted amino group mono- or di-substituted by a $C_{1-4}$ alkyl group, and Z represents a lower alkoxycarbonyl group having 2 to 5 carbon atoms, or Y and Z together form a divalent group —Y—Z— of the following formula

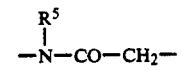

wherein $R^5$ represents an alkyl group having 1 to 4 carbon atoms, or a group of the following formula

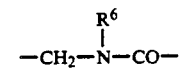

wherein $R^6$ represents an alkyl group having 1 to 4 carbon atoms, or its pharmaceutically acceptable salt with the proviso that X is

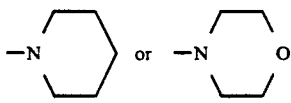

when Y is an amino group or an amino group mono- or di-substituted by $C_{1-4}$ alkyl group.

2. The compound of claim 1 in which the pharmaceutically acceptable salt is selected from the group consisting of hydrochlorides, hydrobromides, sulfates, bisulfites, phosphates, acid phosphates, acetates, maleates, fumarates, succinates, lactates, tartrates, benzoates, citrates, gluconates, glucanates, methanesulfonates, p-toluenesulfonates, naphthalenesulfonates and quaternary ammonium salts of the pyrimidine.

3. A pharmaceutical composition for neurological diseases which comprises as an active ingredient a pyrimidine compound represented by the following formula (I)

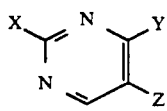     (I)

wherein X represents
(i) a group of the following formula (I)-1

     (I)-1 wherein $R^1$ represents a hydrogen atom or an alkyl group having 1 to 4 carbon atoms, $R^2$ represents a cyclohexyl, phenyl, benzyl or piperidyl group which may be substituted by C1-4 alkyl group, or an alkyl group having 1 to 4 carbon atoms which may be substituted by a piperidino group, or $R^1$ and $R^2$ together with the nitrogen atom to which they are bonded form a heterocyclic ring selected from the group consisting of

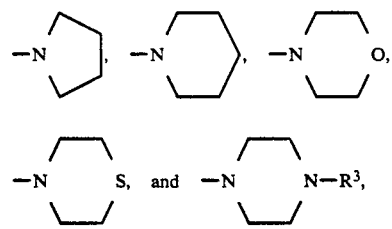

$R^3$ represents an alkylaminocarbonyl group mono- or d-substituted by a $C_{1-6}$ alkyl group, and the heterocyclic group may optionally be mono- to penta-substituted by a $C_{1-4}$ alkyl group, or substituted by a $C_{3-5}$ polymethylene group on the adjoining ring-member carbons, or (ii) a group represented by the following formula (I)-2

$$-S-R^4 \qquad (I)\text{-}2$$

wherein $R^4$ represents an alkyl group having 1 to 4 carbon atoms, Y represents an amino group or a substituted amino group mono- or di-substituted by a $C_{1-6}$ alkyl group, and Z represents methyl group substituted by a $C_{2-5}$ lower alkoxycarbonyl group or a lower alkoxycarbonyl group having 2 to 5 carbon atoms, or Y and Z together form a divalent group —Y—Z— of the following formula

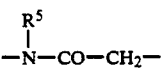

wherein $R^5$ represents an alkyl group having 1 to 4 carbon atoms which may be substituted by a lower alkoxy group, or a group of the following formula

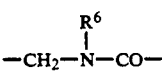

wherein $R^6$ represents an alkyl group having 1 to 4 carbon atoms, or its pharmaceutically acceptable salt, and a pharmaceutically acceptable carrier, with the proviso that X is

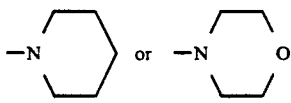

when Y is an amino group or an amino group mono- or di-substituted by $C_{1-4}$ alkyl group.

4. The pharmaceutical composition of claim 3 in which the pharmaceutically acceptable salt is selected from the group consisting of hydrochlorides, hydrobromides, sulfates, bisulfites, phosphates, acid phosphates, acetates, maleates, fumarates, succinates, lactates, tartrates, benzoates, citrates, gluconates, glucanates, methanesulfonates, p-toluenesulfonates, naphthalenesulfonates and quaternary ammonium salts of the pyrimidine.

5. The pyrimidine compound of claim 1 wherein X is the group of formula (I)-1.

6. The pyrimidine compound of claim 5 wherein Y is said amino group or substituted amino group, and Z is lower alkoxycarbonyl group.

7. The pyrimidine compound of claim 5 wherein Z and Y together form the divalent group of formula

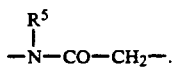

8. The pyrimidine compound of claim 5 wherein Z and Y together form the divalent group of formula

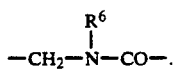

9. The pyrimidine compound of claim 5 wherein $R^1$ represents said hydrogen atom or said alkyl group.

10. The pyrimidine compound of claim 7 wherein $R^1$ represents said hydrogen atom or said alkyl group.

11. The pyrimidine compound of claim 6 wherein X represents (i) said group of the formula (I)-1.

12. The pyrimidine compound of claim 5 wherein $R^1$ and $R^2$ together with the nitrogen atom to which they are bonded form one of said heterocyclic rings (a) to (e).

13. The pyrimidine compound of claim 7 wherein $R^1$ and $R^2$ together with the nitrogen atom to which they are bonded from one of said heterocyclic rings (a) to (e).

14. A pyrimidine represented by the following formula (I)

$$\text{(I)}$$

wherein X represents
(i) a group of the following formula (I)-1

$$\text{(I)-1}$$

wherein $R^1$ represents a hydrogen atom or an alkyl group having 1 to 4 carbon atoms, $R^2$ represents a phenethyl, cyclohexyl, phenyl, benzyl or piperidyl group which may be substituted by a C1–4 alkyl group, or an alkyl group having 1 to 4 carbon atoms which may be substituted by a piperidino group, or $R^1$ and $^2$ together with the nitrogen atom to which they are bonded form a heterocyclic ring selected from the group consisting of (a)

(b)

(c)

(d)

(e)

and (f)

wherein $R^{31}$ and $R^{32}$ are identical or different and each represents a hydrogen atom or a lower alkoxy group, and the heterocyclic group may optionally be substituted by a phenyl, benzyl, phenylthio, cyano or lower alkoxycarbonyl group or monosubstituted by the group or mono- to penta-substituted by a $C_{1-4}$ alkyl group, or substituted by a $C_{3-5}$ polymethylene group on the adjoining ring-member carbons, or (ii) a group represented by the following formula (I)-2

$$-S-R^4 \quad \text{(I)-2}$$

wherein $R^4$ represents an alkyl group having 1 to 4 carbon atoms,

Y represents an amino group or a substituted amino group mono- or di-substituted by a $C_{1-4}$ alkyl group, and Z represents a methyl group substituted by a $C_{2-5}$ alkoxycarbonyl group or a lower alkoxycarbonyl group having 2 to 5 carbon atoms, or Y and Z together form a divalent group —Y—Z— of the following formula $$\begin{array}{c} R^5 \\ | \\ -N-CO-CH_2- \end{array}$$

wherein $R^5$ represents an alkyl group having 1 to 5 carbon atoms which may be substituted by a lower alkoxy group, or a group of the following formula $$\begin{array}{c} R^6 \\ | \\ -CH_2-N-CO- \end{array}$$

wherein $R^6$ represents an alkyl group having 1 to 4 carbon atoms, or its pharmaceutically acceptable salt with the proviso that X is when Y is an amino group or an amino group mono- or di-substituted by $C_{1-4}$ alkyl group.

15. A pyrimidine compound according to claim 14 wherein $R^2$ is cyclohexyl, phenyl, benzyl, piperidyl, piperidyl substituted by a C1–C4 alkyl group, alkyl of 1 to 4 carbon atoms or alkyl of 1 to 4 carbon atoms substituted by a piperidine group.

16. A pyrimidine compound according to claim 14 wherein $R^1$ and $R^2$ together with the nitrogen atom to which they are bonded form one of said heterocyclic rings (a) to (f).

17. The pyrimidine compound according to claim 16 wherein said heterocyclic ring is

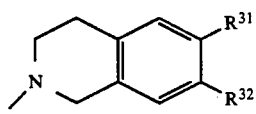

or

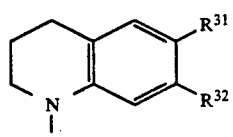

wherein R³¹ and R³² are as defined above.

18. The pyrimidine compound of claim 14 wherein X is the group of formula (I)-2.

19. The pyrimidine compound of claim 1 wherein X is the group of formula (I)-2.

20. The pyrimidine compound of claim 5 which is selected from the group consisting of

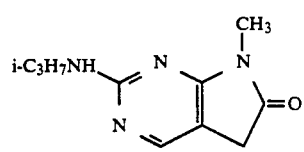 (100)

Hydrochloride of (100) (102)
Maleate of (100) (104)

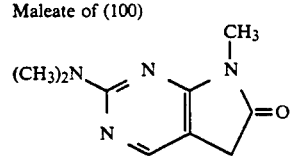 (106)

Maleate of (106) (108)

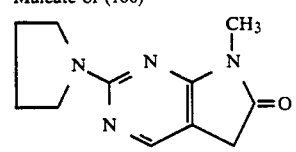 (110)

Maleate of (110) (112)

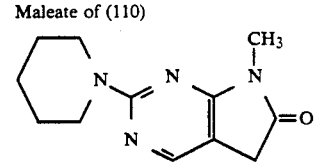 (114)

Hydrochloride of (114) (116)
Maleate of (114) (118)

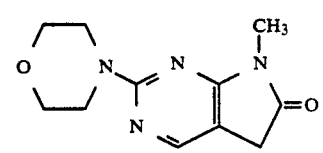 (120)

Hydrochloride of (120) (122)

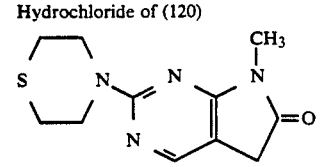 (124)

Hydrochloride of (124) (126)

-continued

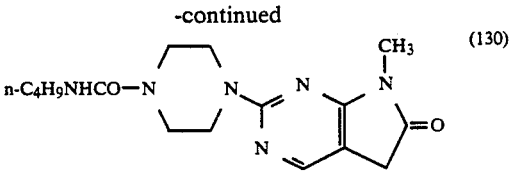 (130)

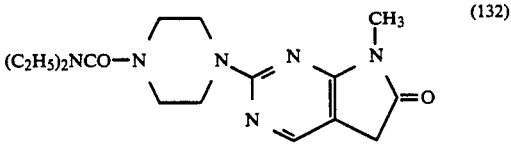 (132)

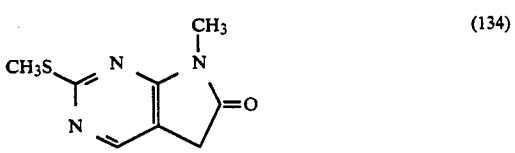 (134)

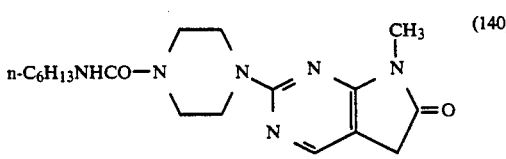 (140)

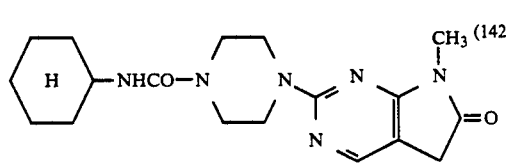 (142)

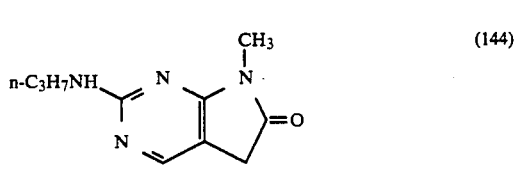 (144)

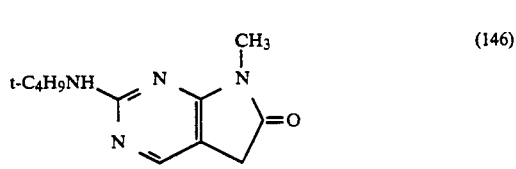 (146)

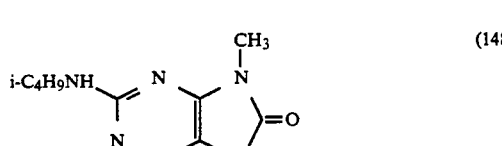 (148)

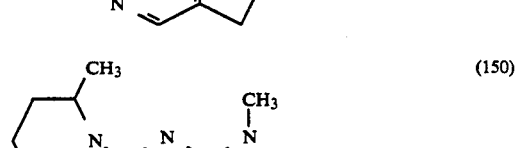 (150)

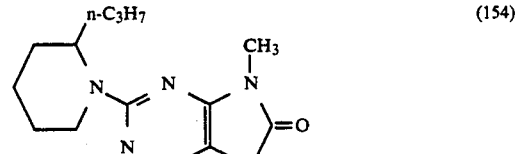 (154)

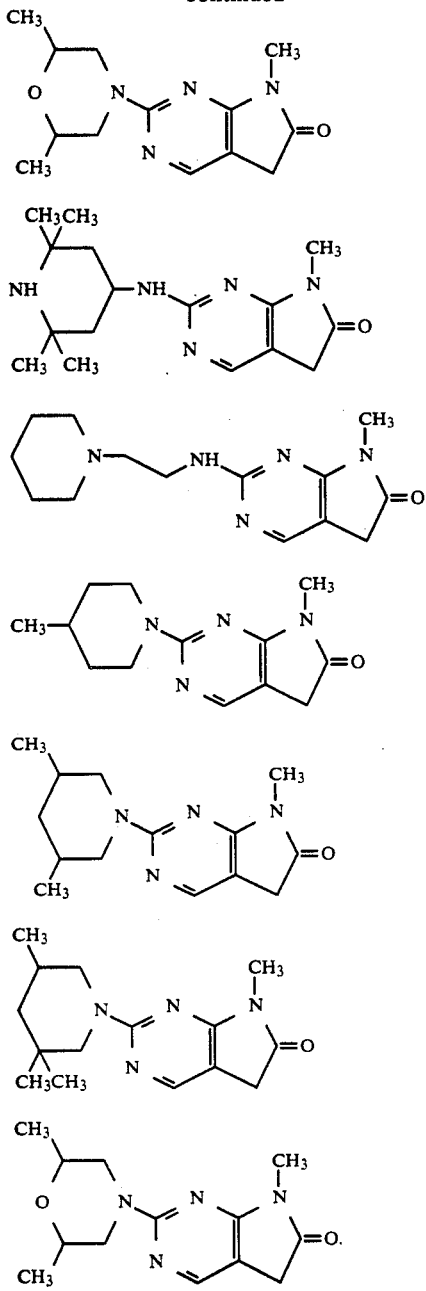
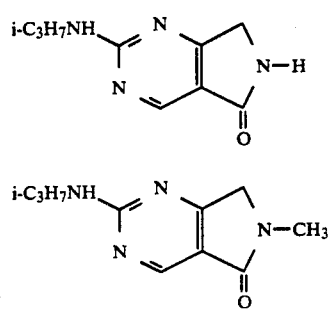
21. The pyrimidine compound of claim 8 which is selected from the group consisting of -continued

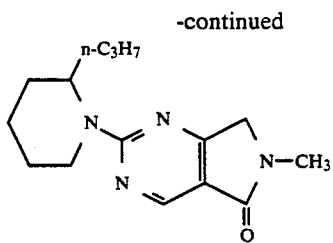
(224)

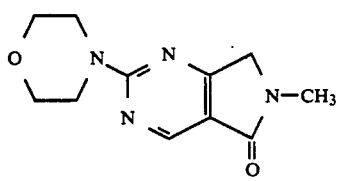
(232)

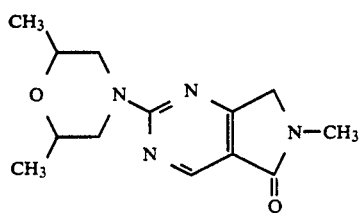
(234)

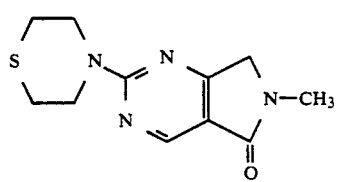
(236)

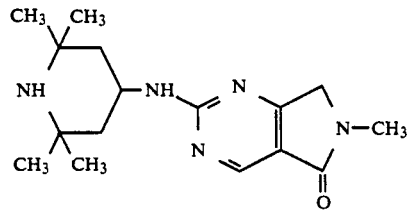
(238)

and

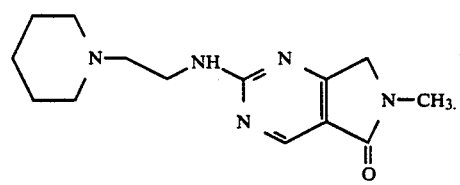
(240)

22. The pyrimidine compound of claim 1 which is selected from the group consisting of

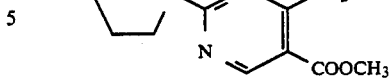
(400)

Hydrochloride of (400) (402)

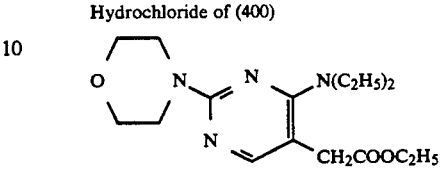
(404)

and

Maleate of (404). (406)

23. A pyrimidine compound represented by the following formula

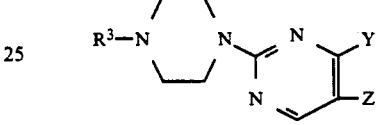

wherein
R³ represents cyclohexyl, 4-pyridyl, a phenyl group which may be substituted by chlorine or a lower alkoxy group, or an alkylamino carbonyl group mono- or di-substituted by a $C_{1-6}$ alkyl group, Y and Z together form a divalent group —Y—Z— of the following formula

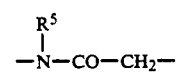

wherein R⁵ represents an alkyl group having 1 to 4 carbon atoms or a group of the following formula

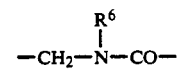

wherein R⁶ represents an alkyl group having 1 to 4 carbon atoms,
or its pharmaceutically acceptable salt.

24. A pyrimidine compound having the formula

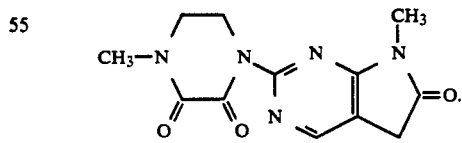

* * * * *